US010105294B2

(12) United States Patent
Imoto

(10) Patent No.: US 10,105,294 B2
(45) Date of Patent: *Oct. 23, 2018

(54) DISPERSION AND METHOD FOR FORMING HYDROGEL

(71) Applicant: NISSAN CHEMICAL INDUSTRIES, LTD., Tokyo (JP)

(72) Inventor: Takayuki Imoto, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/679,432

(22) Filed: Aug. 17, 2017

(65) Prior Publication Data

US 2017/0340526 A1 Nov. 30, 2017

Related U.S. Application Data

(62) Division of application No. 14/904,284, filed as application No. PCT/JP2014/067802 on Jul. 3, 2014, now Pat. No. 9,782,331.

(30) Foreign Application Priority Data

Jul. 9, 2013 (JP) ................. 2013-143791

(51) Int. Cl.
| *A61K 8/04* | (2006.01) |
| *C09K 3/00* | (2006.01) |
| *B01J 13/00* | (2006.01) |
| *A61K 8/64* | (2006.01) |
| *A61Q 19/00* | (2006.01) |
| *A61K 9/06* | (2006.01) |
| *A61K 47/42* | (2017.01) |
| *C07K 5/062* | (2006.01) |
| *C07K 5/083* | (2006.01) |
| *C07K 5/103* | (2006.01) |
| *A61K 8/44* | (2006.01) |
| *A61K 8/34* | (2006.01) |
| *A61K 8/37* | (2006.01) |

(Continued)

(52) U.S. Cl.
CPC ............... *A61K 8/04* (2013.01); *A61K 8/042* (2013.01); *A61K 8/342* (2013.01); *A61K 8/345* (2013.01); *A61K 8/375* (2013.01); *A61K 8/416* (2013.01); *A61K 8/442* (2013.01); *A61K 8/55* (2013.01); *A61K 8/64* (2013.01); *A61K 8/731* (2013.01); *A61K 8/733* (2013.01); *A61K 9/06* (2013.01); *A61K 47/10* (2013.01); *A61K 47/14* (2013.01); *A61K 47/186* (2013.01); *A61K 47/24* (2013.01); *A61K 47/36* (2013.01); *A61K 47/38* (2013.01); *A61K 47/42* (2013.01); *A61Q 19/00* (2013.01); *B01J 13/00* (2013.01); *B01J 13/0052* (2013.01); *C07K 5/06026* (2013.01); *C07K 5/0806* (2013.01); *C07K 5/1008* (2013.01); *C09K 3/00* (2013.01); *A61K 2800/10* (2013.01); *A61K 2800/48* (2013.01); *A61K 2800/52* (2013.01); *A61K 2800/5922* (2013.01); *A61K 2800/805* (2013.01)

(58) Field of Classification Search
CPC .............. C07K 5/06026; C07K 5/0806; C07K 5/1008; B01J 13/0052; B01J 13/00; B01J 13/0065; A61K 8/04; A61K 8/042; A61K 47/42; A61K 47/186; A61K 8/64; C09K 2003/1034; C09K 2003/1071; C09K 3/00; C09H 7/00

See application file for complete search history.

(56) References Cited

U.S. PATENT DOCUMENTS

| 5,385,688 A | 1/1995 | Miller et al. |
| 2010/0279955 A1* | 11/2010 | Miyachi ................. A61K 8/042 514/21.9 |
| 2011/0183913 A1 | 7/2011 | Miyamoto et al. |
| 2012/0258059 A1 | 10/2012 | Iwama et al. |
| 2014/0113976 A1 | 4/2014 | Matsumoto et al. |

FOREIGN PATENT DOCUMENTS

| EP | 2172475 A1 | 4/2010 |
| EP | 2319894 A1 | 5/2011 |

(Continued)

OTHER PUBLICATIONS

Suzuki et al, "Supramolecular Hydrogels Formed by L-Lysine Derivatives," Chemistry Letters, vol. 33, No. 11, 2004, pp. 1496-1497.
Jung et al, Self Assembly of a Sugar-Based Gelator in Water: Its Remarkable Diversity in Gelation Ability and Aggregate Structure, Langmuir, vol. 17, 2001, pp. 7229-7232.
Hamachi et al, Solid-phase lipid synthesis (SPLS)-2: incidental discovery of organogelators based on artificial glycolipids, Tetrahedron Letters, vol. 42, 2001, pp. 6141-6145.

(Continued)

*Primary Examiner* — Yate' K Cutliff
(74) *Attorney, Agent, or Firm* — Oliff PLC

(57) ABSTRACT

An object is to provide dispersion containing lipid peptide type compound useful as low molecular weight gelator, such as lipid dipeptide and lipid tripeptide, and dissolution accelerator capable of dissolving the lipid peptide type compound at lower temperature and more easily. It is also an object to provide dispersion that can form hydrogel by simpler method and under milder condition (low temperature) and from which gel can be obtained as gel having high thermal stability, and provide method for forming the gel. Dispersion including: a lipid peptide type compound in which peptide portion formed by repetition of at least two or more identical or different amino acids is bonded to lipid portion including $C_{10-24}$ aliphatic group; dissolution accelerator having, in molecules thereof, hydrophilic portion and hydrophobic portion, the hydrophilic portion having betaine structure; and water; and method for producing hydrogel by use of the dispersion.

16 Claims, No Drawings

(51) Int. Cl.
*A61K 8/41* (2006.01)
*A61K 8/55* (2006.01)
*A61K 8/73* (2006.01)
*A61K 47/10* (2017.01)
*A61K 47/14* (2017.01)
*A61K 47/18* (2017.01)
*A61K 47/24* (2006.01)
*A61K 47/36* (2006.01)
*A61K 47/38* (2006.01)

(56) References Cited

FOREIGN PATENT DOCUMENTS

| EP | 2700691 A1 | 2/2014 |
|---|---|---|
| JP | 2002-047172 A | 2/2002 |
| JP | 2007-209874 A | 8/2007 |
| JP | 2011-036760 A | 2/2011 |
| JP | 2012-030221 A | 2/2012 |
| WO | 2009/005151 A1 | 1/2009 |
| WO | 2009/005152 A1 | 1/2009 |
| WO | 2011/052613 A1 | 5/2011 |
| WO | 2012/133787 A1 | 10/2012 |
| WO | 2012/144609 A1 | 10/2012 |
| WO | 2014003015 A1 | 1/2014 |
| WO | 2014054699 A1 | 4/2014 |
| WO | WO 2014/054702 * | 4/2014 ............... A61K 9/06 |

OTHER PUBLICATIONS

Suzuki et al, Supramolecular hydrogel formed by glucoheptonamide of L-lysine: simple preparatin and excellent hydrogelation ability, Tetrahedron, vol. 63, 2007, pp. 7302-7308.

Matsuzawa et al, Assembly and Photoinduced Organization of Mono- and Oligopeptide Molecules Containing an Azobenzene Moiety, Advanced Functional Matter, vol. 17, pp. 1507-1514.

Oct. 7, 2014 International Search Report issued in International Patent Application No. PCT/JP2014/067802.

Sep. 9, 2016 Office Action Issued in U.S. Appl. No. 14/904,284.

Nov. 9, 2016 Extended Search Report issued in European Patent Application No. 14822909.9.

Mar. 17, 2017 Office Action Issued in U.S. Appl. No. 14/904,284.

* cited by examiner

DISPERSION AND METHOD FOR FORMING HYDROGEL

This is a Divisional of application Ser. No. 14/904,284 filed Jan. 11, 2016, which is a national stage application of PCT/JP2014/067802 filed Jul. 3, 2014, which claims the benefit of JP 2013-143791. The entire disclosures of the prior applications are hereby incorporated by reference herein their entireties.

TECHNICAL FIELD

The present invention relates to a dispersion containing a low molecular weight lipid peptide type compound useful as a thickener or a gelator, and a method for forming a hydrogel using the dispersion.

BACKGROUND ART

A hydrogel contains water as a solvent and thus is useful as a gel having high biocompatibility. Such a hydrogel is used in various fields such as applications for commodities such as paper diapers, cosmetics and aromatics.

Examples of a conventional hydrogel include polymer gels formed through such steps that polymer chains are cross-linked to form a three-dimensional network structure, and that a noncovalent bond is formed between the three-dimensional network structure and the solvent such as water, so that the three-dimensional network structure swells to form a polymer gel. Many studies for the physical properties of the polymer gel and many developments of the applications of the polymer gel have been performed with respect to natural polymer gels formed from polysaccharide such as agarose and protein, and synthetic polymer gels in which polymer chains are cross-linked to each other through a chemical covalent bond, such as an acrylamide gel.

Recently, besides the above gels containing polymer compounds, hydrogels formed by the self-assembly of an organic compound having a relatively low molecular weight have been found and various hydrogels have been studied.

The formation of the gel by the self-assembly of a low molecular weight compound has been elucidated to occur through the following steps: in a substances (low molecular weight compounds) group in a random state at first, molecules of the substances associate spontaneously while they are having directionality by, for example, an intermolecular non-covalent interaction between the molecules of the substances under an appropriate external condition (in a medium) to form a macro molecule-assembly; and plural macro molecule-assemblies form a network and the network swells with a surrounding solvent to form a gel. Examples of a driving force for this molecule association (self-assembly) include a force by an action of a hydrogen bond having a relatively weak bonding strength, and a force by a van der Waals interaction (non-hydrogen bond) having a bonding strength even weaker than that of the hydrogen bond.

Many of the low molecular weight gelators that have been disclosed are an amphipathic compound having a combination of a hydrophobic portion of a long-chain alkyl group and a hydrophilic portion. Examples thereof include an amphipathic compound in which the hydrophilic portion is an amino acid [Non-patent Document 1], an amphipathic compound in which the hydrophilic portion is a peptide [Patent Documents 1 and 2], an amphipathic compound in which the hydrophilic portion is a monosaccharide or a polysaccharide [Non-patent Documents 2 and 3], and an amphipathic compound in which the hydrophilic portion is a polyol [Non-patent Document 4]. In addition, there has also been disclosed a low molecular weight gelator utilizing such a tendency that a peptide made up with valine easily takes a β-sheet structure [Non-patent Document 5].

Such a low molecular weight hydrogelator can form a hydrogel by a method including: heating and stirring the hydrogelator and water as the solvent under a temperature condition of about 100° C. to dissolve and disperse the gelator in water, and leaving the resultant solution to stand still at room temperature.

PRIOR ART DOCUMENTS

Patent Documents

Patent Document 1: International Publication No. WO 2009/005151 pamphlet
Patent Document 2: International Publication No. WO 2009/005152 pamphlet

Non-Patent Documents

Non-patent Document 1: Suzuki, Masahiro. Yumoto, Mariko. Mutsumi, Shirai. Hirofusa, Hanabusa, Kenji. Chemistry Letters, 33(11), 1496-1497
Non-patent Document 2: Jong Hwa Jung, Georeg John, Mitsutosish Mausda, Kaname Yoshida, Seiji Shinnkai, and Toshimi Shimizu Langumir 2001, 17, 7229-7232
Non-patent Document 3: I. Hamachi, S. Kiyonaka, S. Shinkai, Tetrahedron Lett., 2001, 42, 6141. I. Hamachi, S. Kiyonaka, S. Shinaki, Chem. Commun., 2000, 1281
Non-patent Document 4: Masahiro Suzuki, Sanae Owa, Hirofusa Shirai and Kenji Hanabusa, Tetrahedron 2007 63 7302-7308
Non-patent Document 5: Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514

SUMMARY OF THE INVENTION

Problem to be Solved by the Invention

It is an object of the present invention to provide a dispersion containing a lipid peptide type compound useful as a low molecular weight gelator, such as a lipid dipeptide and a lipid tripeptide, and a dissolution accelerator capable of dissolving the lipid peptide type compound at a lower temperature and more easily.

It is also an object of the present invention to provide a dispersion that can form a hydrogel by a simpler method and under a milder condition (low temperature) and from which a gel can be obtained as a gel having high thermal stability, and provide a method for forming the gel.

Means for Solving the Problems

As a result of assiduous research intended to overcome these disadvantages, the inventors of the present invention have found that a lipid peptide type compound containing a low molecular weight lipid peptide or a pharmaceutically usable salt thereof exhibits high solubility and high dispersibility relative to a solvent including a dissolution accelerator having, in molecules thereof, a hydrophilic portion and a hydrophobic portion under a condition of a temperature lower than a temperature in the case of a conventional lipid peptide type compound, and forms a dispersion suitable as a premix raw material for a gel or a thickener for an antifreezing fluid.

The inventors of the present invention have also found that by adding a polymer emulsifier to the dispersion in which the lipid peptide type compound is dissolved in the solvent, upon preparing a gel using the dispersion, even when the heated gelator dispersion is subjected to stirring-cooling down, a gel can be satisfactorily formed, and that the dispersion is useful as a premix for a gel applicable to cosmetics or quasi-drugs. The inventors of the present invention have further found that by adding a heat resistance improver to the dispersion, high thermal stability can be imparted to the gel obtained using the dispersion, and have completed the present invention.

The inventors of the present invention have further found that by using a dissolution accelerator, a satisfactory gel can be formed even when reducing the adding amount of the lipid peptide type compound necessary for gelation and containing a low molecular weight lipid peptide or a pharmaceutically usable salt thereof.

Specifically, the present invention relates to, according to a first aspect, a dispersion comprising: a lipid peptide type compound in which a peptide portion formed by repetition of at least two or more identical or different amino acids is bonded to a lipid portion including a $C_{10-24}$ aliphatic group; a dissolution accelerator having, in molecules thereof, a hydrophilic portion and a hydrophobic portion, the hydrophilic portion having a betaine structure; and water.

The present invention relates to, according to a second aspect, the dispersion according to the first aspect, characterized in that the lipid peptide type compound contains at least one of compounds of Formula (1) to Formula (3) and pharmaceutically usable salts of the compounds:

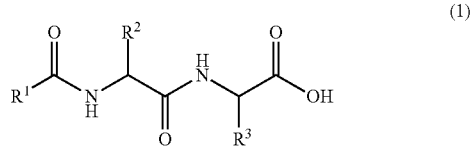

(1)

(where $R^1$ is a $C_{9-23}$ aliphatic group; $R^2$ is a hydrogen atom or a $C_{1-4}$ alkyl group optionally having a $C_{1-2}$ branching chain; $R^3$ is a $—(CH_2)_n—X$ group; n is a number of 1 to 4; and X is an amino group, a guanidino group, a $—CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s)),

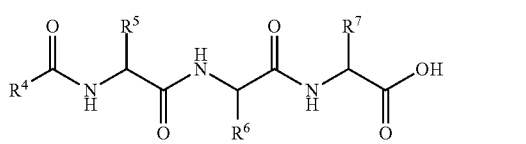

(2)

(where $R^4$ is a $C_{9-23}$ aliphatic group; $R^5$ to $R^7$ are each independently a hydrogen atom, a $C_{1-4}$ alkyl group optionally having a $C_{1-2}$ branching chain, or a $—(CH_2)_n—X$ group; n is a number of 1 to 4; X is an amino group, a guanidino group, a $—CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s)), and

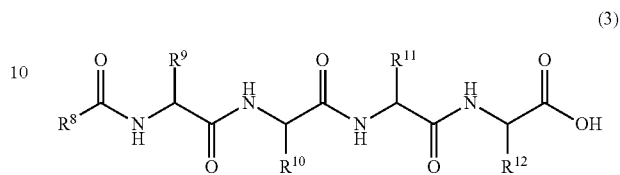

(3)

(where $R^8$ is a $C_{9-23}$ aliphatic group; $R^9$ to $R^{12}$ are each independently a hydrogen atom, a $C_{1-4}$ alkyl group optionally having a $C_{1-2}$ branching chain, or a $—(CH_2)_n—X$ group; n is a number of 1 to 4; X is an amino group, a guanidino group, a $—CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s)).

The present invention relates to, according to a third aspect, the dispersion according to the first aspect or the second aspect, further comprising a polyhydric alcohol.

The present invention relates to, according to a fourth aspect, the dispersion according to the third aspect, in which the dissolution accelerator is at least one selected from lauryldimethyl aminoacetic acid betaine, lauramidopropyl betaine, lauryl hydroxy sulfobetaine, stearyl betaine, and lysophosphatidylcholine.

The present invention relates to, according to a fifth aspect, the dispersion according to any one of the first aspect to the fourth aspect, further comprising a polymer emulsifier, in which the lipid peptide type compound serves as a gelator.

The present invention relates to, according to a sixth aspect, the dispersion according to the fifth aspect, in which the dispersion is a premix for preparing a cosmetic or a quasi-drug.

The present invention relates to, according to a seventh aspect, the dispersion according to any one of the first aspect to the fourth aspect, in which the dispersion is used as a thickener for an antifreezing fluid.

The present invention relates to, according to an eighth aspect, the dispersion according to the fifth aspect or the sixth aspect, in which the polymer emulsifier is at least one polymer compound selected from the group consisting of a graft polymer compound in which a hydrophobic moiety is grafted to a hydrophilic backbone and a block polymer compound containing a hydrophobic structural unit and a hydrophilic structural unit.

The present invention relates to, according to a ninth aspect, the dispersion according to the eighth aspect, further comprising a heat resistance improver.

The present invention relates to, according to a tenth aspect, the dispersion according to the ninth aspect, in which the heat resistance improver is at least one higher alcohol selected from the group consisting of $C_{10-20}$ saturated and unsaturated higher alcohols or at least one higher fatty acid ester selected from the group consisting of $C_{10-20}$ saturated and unsaturated higher fatty acid esters.

The present invention relates to, according to an eleventh aspect, the dispersion according to the tenth aspect, in which the heat resistance improver is cetanol, myristyl alcohol, or glyceryl monostearate.

The present invention relates to, according to a twelfth aspect, the dispersion according to the eighth aspect, in which the polymer compound is selected from the group consisting of a carboxymethyl cellulose and an alginic acid ester.

The present invention relates to, according to a thirteenth aspect, the dispersion according to the twelfth aspect, in which the polymer compound is propylene glycol alginate.

The present invention relates to, according to a fourteenth aspect, a method for producing a hydrogel, the method comprising: adding the dispersion as described in any one of the fifth aspect and the sixth aspect, and the eighth aspect to the thirteenth aspect to water and heating the resultant mixture to a temperature that is room temperature or higher and lower than 100° C.; and cooling down the mixture with stirring until the temperature of the mixture reaches a temperature lower than the temperature in the heating to form a gel.

The present invention relates to, according to a fifteenth aspect, a hydrogel formed using the dispersion as described in any one of the fifth aspect and the sixth aspect, and the eighth aspect to the thirteenth aspect.

Effects of the Invention

The dispersion of the present invention can be prepared by stirring the lipid peptide type compound and a dissolution accelerator or the like under a relatively mild temperature condition such as at 80° C. to dissolve and disperse the lipid peptide type compound within a relatively short time. The dispersion of the present invention is a dispersion suitable as a premix raw material for a gel or a thickener for an antifreezing fluid.

A polymer emulsifier may be added to the dispersion of the present invention. This can provide a satisfactory hydrogel without forming insoluble matters or deposits in the preparation of a gel using the dispersion under a mild temperature condition such as at 80° C. and even while the dispersion is stirred and cooled down. A polyhydric alcohol may be blended in the dispersion of the present invention. This can provide a satisfactory hydrogel using an even smaller amount of the lipid peptide type compound (gelator). The dispersion is useful as a premix for a gel applicable to cosmetics or quasi-drugs.

Furthermore, a heat resistance improver may be added to the dispersion of the present invention. This can impart high thermal stability to the gel formed using the dispersion.

The lipid peptide type compound contained in the dispersion of the present invention is an artificial low molecular weight compound composed only of a lipid and a peptide having an extremely high degree of safety. Phospholipids, biosurfactants, fatty acids or salts thereof, and surfactants serving as the dissolution accelerator having, in molecules thereof, a hydrophilic portion and a hydrophobic portion, higher alcohols serving as the heat resistance improver, polyhydric alcohols used for the mixed solvent of the dispersion, and other contents are additives applicable to foods, cosmetics, and medicines. That is, the dispersion of the present invention has a high degree of biological safety and particularly, from the viewpoint of safety required for a cell culture base material, medical materials, materials for cosmetics, or the like, the dispersion of the present invention is useful in the above applications.

Furthermore, the dispersion of the present invention can form a gel by gelling water without using a cross-linking agent or the like required during the formation of, for example, a synthetic polymer type gel that has been conventionally disclosed. Thus, no unreacted substance such as an unreacted cross-linking agent remains in the obtained hydrogel, for example. Moreover, the lipid peptide type compound contained in the dispersion can form a hydrogel only with a small adding amount of around 1% by mass, and applies low load to the environment and the organism when the lipid peptide type compound is incorporated into them.

The method for producing a hydrogel of the present invention can form a gel under a relatively mild condition such as at lower than 100° C. and even while the heated gelator dispersion is stirred. Even when an additive for cosmetics or an additive for quasi-drugs for which influences of heat on these additives are desired to be eliminated as much as possible, is added to the dispersion, the method for forming a hydrogel of the present invention can form a hydrogel without degenerating these additives.

The gel of the present invention can be obtained by adding a smaller amount of a gelator than that for a conventional gel as described above, so that it can be mentioned that the gel of the present invention is a gel having a high degree of safety both in the organism and in the environment.

Furthermore, as described above, when a gel obtained from a lipid peptide that is a low molecular weight compound is used in an external environment, for example in the soil, the gel is easily decomposed by soil bacteria or the like, or when the gel is used in an organism, the gel is easily decomposed by metabolic enzyme, so that it applies low load to the environment and the organism.

The gel of the present invention is a gel that is capable of being formed under a relatively mild condition and to which additives that may be influenced by heat, can be blended.

MODES FOR CARRYING OUT THE INVENTION

Hereinafter, the present invention is described in detail including the circumstances leading to the completion of the present invention.

A conventionally disclosed low molecular weight gelator, for example, a gelator containing as the hydrophilic portion, a peptide (a lipid peptide, in Patent Documents 1 and 2) exhibits low solubility in a solvent, so that for causing the gelator to gel a solvent, it is necessary that first, a solvent desired to be gelled is heated to a high temperature such as 100° C. to dissolve and disperse the gelator in the solvent.

The above lipid peptide low molecular weight gelator is regarded as being able to complete the gel formation by forming a macro molecular assembly through a weak interaction (van der Waals interaction and the like) between the molecules and destruction of such a molecular assembly hinders the gel formation. Therefore, it is necessary for the gel formation that a gelator dispersion prepared by heating the solvent at a high temperature be left still while the gelator dispersion is cooled down. When the gelator dispersion is stirred during the cooling down, the gel formation may not be caused.

According to such circumstances, the inventors of the present invention have found an object of providing a material capable of forming a gel under a milder temperature condition, for example, at a temperature of lower than 100° C. and capable of forming a gel even while the heated gelator dispersion is stirred during cooling down of the dispersion.

Then, for such an object, the inventors of the present invention have studied a method for forming a gel by: dissolving and dispersing temporarily a lipid peptide type compound in a composition that accelerates dissolution of the compound to prepare a solution (dispersion); and blending the solution (dispersion) as what is called a premix of a gelation material in a solvent (such as water).

First, when the inventors of the present invention have studied a dissolution accelerator having high solubility capable of dissolving a lipid peptide type compound in a high concentration, particularly having a high degree of safety by which the use of the dissolution accelerator for quasi-drugs, cosmetics, and the like is acceptable, they have found that a compound having, in molecules thereof, a hydrophilic portion having a betaine structure and a hydrophobic portion is suitable therefor.

Subsequently, when the inventors of the present invention have variously studied for enabling the gel formation using the above premix at a low temperature with stirring, they have found that by blending a polymer emulsifier such as an alginic acid ester in the premix, the solubility and the dispersibility of the premix and the strength of the gel when the premix is blended in a solvent can be secured, and by blending a heat resistance improver such as a higher alcohol or a higher fatty acid ester in the premix, the heat resistance of the formed gel can be improved.

According to the above circumstances, the inventors of the present invention have completed the present invention.

<Dispersion>

The dispersion of the present invention contains a mixed solution including a lipid peptide type compound in which a peptide portion formed by repetition of at least two or more identical or different amino acids is bonded to a lipid portion including a $C_{10-24}$ aliphatic group; a dissolution accelerator having, in molecules thereof, a hydrophilic portion having a betaine structure and a hydrophobic portion; and water.

[Lipid Peptide Type Compound]

As the lipid peptide type compound in the dispersion of the present invention, a compound (lipid peptide) of Formula (1) below to Formula (3) below or a pharmaceutically usable salt thereof (a low molecular weight compound having a lipid portion that is a hydrophobic portion and a peptide portion that is a hydrophilic portion) can be used.

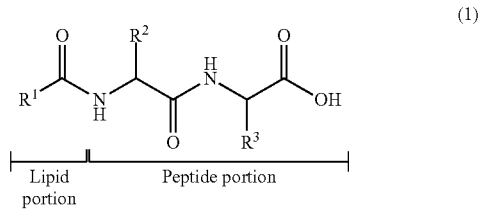

(1)

In Formula (1), $R^1$ is a $C_{9-23}$ aliphatic group, preferably a linear $C_{11-23}$ aliphatic group optionally having 0 to 2 unsaturated bonds.

Specific examples of the lipid portion (acyl group) composed of $R^1$ and a carbonyl group adjacent to $R^1$ include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an cicosylcarbonyl group, a behenoyl group, an erucanoyl group, a docosylcarbonyl group, a lignoceroyl group, and a nervonoyl group and particularly preferred examples thereof include a lauroyl group, a myristoyl group, a palmitoyl group, a margaroyl group, a stearoyl group, an oleoyl group, an elaidoyl group, and a behenoyl group.

In Formula (1), $R^2$ contained in the peptide portion is a hydrogen atom or a $C_{1-4}$ alkyl group optionally having a $C_{1-2}$ branching chain.

The $C_{1-4}$ alkyl group optionally having a $C_{1-2}$ branching chain means an alkyl group in which the number of carbon atoms of the backbone is 1 to 4 and that may have a $C_{1-2}$ branching chain, and specific examples thereof include methyl group, ethyl group, n-propyl group, isopropyl group, n-butyl group, isobutyl group, sec-butyl group, and tert-butyl group.

$R^2$ is preferably a hydrogen atom or a $C_{1-3}$ alkyl group optionally having a $C_1$ branching chain and more preferably a hydrogen atom.

The $C_{1-3}$ alkyl group optionally having a $C_1$ branching chain means an alkyl group in which the number of carbon atoms of the backbone is 1 to 3 and that may have a $C_1$ branching chain, and specific examples thereof include methyl group, ethyl group, n-propyl group, isopropyl group, isobutyl group, and sec-butyl group, and among them, preferred are methyl group, isopropyl group, isobutyl group, and sec-butyl group.

In Formula (1), $R^3$ is a $-(CH_2)_n-X$ group. In the $-(CH_2)_n-X$ group, n is a number of 1 to 4 and X is an amino group, a guanidino group, a $-CONH_2$ group, or a 5-membered ring or a 6-membered ring optionally having 1 to 3 nitrogen atom(s), or a fused heterocyclic ring composed of a 5-membered ring and a 6-membered ring optionally having 1 to 3 nitrogen atom(s).

In the $-(CH_2)_n-X$ group as $R^3$, X is preferably an amino group, a guanidino group, a carbamoyl group (a $-CONH_2$ group), a pyrrole group, an imidazole group, a pyrazole group, or an indole group, and more preferably an imidazole group. In the $-(CH_2)_n-X$ group, n is preferably 1 or 2 and more preferably 1.

Accordingly, the $-(CH_2)_n-$ group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrolemethyl group, a 4-imidazolemethyl group, a pyrazolemethyl group, or a 3-indolemethyl group, and more preferably a 4-aminobutyl group, a carbamoylmethyl group, a 2-carbamoylethyl group, a 3-guanidinobutyl group, a 4-imidazolemethyl group, a 3-indolemethyl group, further preferably a 4-imidazolemethyl group.

In the compound of Formula (1), as a lipid peptide particularly preferred as the lipid peptide type compound, there can be mentioned the compounds formed from the following lipid portions and peptide portions (amino acid-assembled portion). Here, the abbreviated names of the amino acids are as follows: alanine (Ala); asparagine (Asn); glutamine (Gln); glycine (Gly); histidine (His); isoleucine (Ile); leucine (Leu); lysine (Lys); tryptophan (Trp); and valine (Val).

Lauroyl-Gly-His, Lauroyl-Gly-Gln, Lauroyl-Gly-Asn, Lauroyl-Gly-Trp, Lauroyl-Gly-Lys, Lauroyl-Ala-His, Lauroyl-Ala-Gln, Lauroyl-Ala-Asn, Lauroyl-Ala-Trp, Lauroyl-Ala-Lys; Myristoyl-Gly-His, Myristoyl-Gly-Gln, Myristoyl-Gly-Asn, Myristoyl-Gly-Trp, Myristoyl-Gly-Lys, Myristoyl-Ala-His, Myristoyl-Ala-Gln, Myristoyl-Ala-Asn, Myristoyl-Ala-Trp, Myristoyl-Ala-Lys; Palmitoyl-Gly-His, Palmitoyl-Gly-Gln, Palmitoyl-Gly-Asn, Palmitoyl-Gly-Trp, Palmitoyl-Gly-Lys, Palmitoyl-Ala-His, Palmitoyl-Ala-Gln, Palmitoyl-Ala-Asn, Palmitoyl-Ala-Trp, Palmitoyl-Ala-Lys; Stearoyl-Gly-His, Stearoyl-Gly-Gln, Stearoyl-Gly-Asn, Stearoyl-Gly-Trp, Stearoyl-Gly-Lys, Stearoyl-Ala-His, Stearoyl-Ala-Gln, Stearoyl-Ala-Asn, Stearoyl-Ala-Trp, Stearoyl-Ala-Lys.

Among them, most preferred are Lauroyl-Gly-His, Lauroyl-Ala-His-Myristoyl-Gly-His, Myristoyl-Ala-His, Palmitoyl-Gly-His, Palmitoyl-Ala-His, Stearoyl-Gly-His, and Stearoyl-Ala-His.

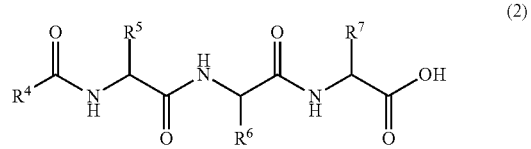

(2)

In Formula (2), R is a $C_{9-23}$ aliphatic group and preferred specific examples thereof include the same groups as defined with respect to $R^1$ above.

In Formula (2), $R^5$ to $R^7$ are each independently a hydrogen atom, a $C_{1-4}$ alkyl group optionally having a $C_{1-2}$ branching chain, or a $—(CH_2)_n—X$ group and at least one of $R^5$ to $R^7$ is a $—(CH_2)_n—X$ group. n is a number of 1 to 4 and X is an amino group, a guanidino group, a $—CONH_2$ group, or a 5-membered ring or a 6-membered ring optionally having 1 to 3 nitrogen atom(s), or a fused heterocyclic ring composed of a 5-membered ring and a 6-membered ring optionally having 1 to 3 nitrogen atom(s). Here, preferred specific examples of $R^5$ to $R^7$ include the same groups as defined with respect to $R^2$ and $R^3$ above.

In the compound of Formula (2), as a preferred lipid peptide, there can be mentioned the compounds formed from the following lipid portions and peptide portions (amino acid-assembled portion).

Myristoyl-Gly-Gly-His, Myristoyl-Gly-Gly-Gln, Myristoyl-Gly-Gly-Asn, Myristoyl-Gly-Gly-Trp, Myristoyl-Gly-Gly-Lys, Myristoyl-Gly-Ala-His, Myristoyl-Gly-Ala-Gln, Myristoyl-Gly-Ala-Asn, Myristoyl-Gly-Ala-Trp, Myristoyl-Gly-Ala-Lys, Myristoyl-Ala-Gly-His, Myristoyl-Ala-Gly-Gln, Myristoyl-Ala-Gly-Asn, Myristoyl-Ala-Gly-Trp, Myristoyl-Ala-Gly-Lys, Myristoyl-Gly-His-Gly, Myristoyl-His-Gly-Gly, Palmitoyl-Gly-Gly-His, Palmitoyl-Gly-Gly-Gln, Palmitoyl-Gly-Gly-Asn, Palmitoyl-Gly-Gly-Trp, Palmitoyl-Gly-Gly-Lys, Palmitoyl-Gly-Ala-His, Palmitoyl-Gly-Ala-Gln, Palmitoyl-Gly-Ala-Asn, Palmitoyl-Gly-Ala-Trp, Palmitoyl-Gly-Ala-Lys, Palmitoyl-Ala-Gly-His, Palmitoyl-Ala-Gly-Gln, Palmitoyl-Ala-Gly-Asn, Palmitoyl-Ala-Gly-Trp, Palmitoyl-Ala-Gly-Lys, Palmitoyl-Gly-His-Gly, Palmitoyl-His-Gly-Gly.

Among them, most preferred are Lauroyl-Gly-Gly-His, Myristoyl-Gly-Gly-His, Palmitoyl-Gly-Gly-His, Palmitoyl-Gly-His-Gly, Palmitoyl-His-Gly-Gly, and Stearoyl-Gly-Gly-His.

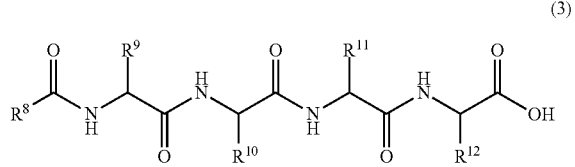

(3)

In Formula (3), $R^8$ is a $C_{9-23}$ aliphatic group and preferred specific examples thereof include the same groups as defined with respect to $R^1$ above.

In Formula (3), $R^9$ to $R^{12}$ are each independently a hydrogen atom, a $C_{1-4}$ alkyl group optionally having a $C_{1-2}$ branching chain, or a $—(CH_2)_n—X$ group and at least one of $R^9$ to $R^{12}$ is a $—(CH_2)_n—X$ group. n is a number of 1 to 4 and X is an amino group, a guanidino group, a $—CONH_2$ group, or a 5-membered ring or a 6-membered ring optionally having 1 to 3 nitrogen atom(s), or a fused heterocyclic ring composed of a 5-membered ring and a 6-membered ring optionally having 1 to 3 nitrogen atom(s). Here, preferred specific examples of $R^9$ to $R^{12}$ include the same groups as defined with respect to $R^2$ to $R^3$ above.

Accordingly, in the compound of Formula (3), as a lipid peptide particularly preferred as the preferred lipid peptide type compound, there can be mentioned Lauroyl-Gly-Gly-Gly-His, Myristoyl-Gly-Gly-Gly-His, Palmitoyl-Gly-Gly-Gly-His, Palmitoyl-Gly-Gly-His-Gly, Palmitoyl-Gly-His-Gly-Gly, Palmitoyl-His-Gly-Gly-Gly, and Stearoyl-Gly-Gly-Gly-His.

In the present invention, a blending amount of the lipid peptide type compound is, for example 0.01% by mass to 30% by mass, preferably 0.05% by mass to 10% by mass, and more preferably 0.0.5% by mass to 5% by mass, based on the total mass of the obtained hydrogel.

In the present invention, a blending amount of the lipid peptide type compound is, for example 0.1% by mass to 40% by mass, preferably 0.1% by mass to 30% by mass, and more preferably 0.1% by mass to 10% by mass, based on the total mass of the obtained dispersion.

The lipid peptide type compound used in the present invention contains at least one of compounds (lipid peptide) of Formula (1) below to Formula (3) below and pharmaceutically usable salts thereof, and when the lipid peptide type compound is used as the hydrogelator, these compounds may be used individually or in combination of two or more types thereof.

[Dissolution Accelerator]

The dissolution accelerator used for a dispersant in the present invention is a compound having, in molecules thereof, a hydrophilic portion and a hydrophobic portion, and the hydrophilic portion has a betaine structure (hereinafter may be called a betaine-based compound).

As the above betaine-based compound, betaine-based compounds known as amphoteric surfactants can be used, for example, such as: N-alkyl-N,N-dimethyl amino acid betaines such as lauryldimethyl aminoacetic acid betaine (lauryl betaine); fatty acid amide alkyl-N,N-dimethyl amino acid betaines such as cocamidopropyl betaine and lauramidopropyl betaine; imidazoline-type betaines such as sodium cocoamphoacetate and sodium lauroamphoacetate; alkylsulfo betaines such as lauryl hydroxy sulfobetaine and alkyl dimethyl taurine; sulfuric acid-type betaines such as alkyl dimethyl amino ethanol sulfuric acid ester; and phosphoric acid-type betaines such as alkyl dimethyl amino ethanol phosphoric acid ester.

Examples of the betaine-based compound include: glycerophospholipids such as phosphatidylcholine, phosphatidyl ethanolamine, phosphatidylserine, phosphatidylinositol, phosphatidylglycerol, diphosphatidylglycerol (cardiolipin), and phosphatidic acid; lyzoglycerophospholipids such as lysophosphatidylcholine (lysolecithin), lysophosphatidylethanolamine, lyzophosphatidylserine, lyzophosphatidylinositol, lyzophosphatidylglycerol, and lysophosphatidic acid; sphingophospholipids such as sphingomyelin; and hydrogenated products thereof. These phospholipids may be those derived from animals and plants such as soy beans and egg yolk or may be synthesized by chemical or enzymatic processes.

Among the betaine-based compounds, preferred examples include lauryldimethyl aminoacetic acid betaine, lauramidopropyl betaine, lauryl hydroxy sulfobetaine, stearyl betaine, lysophosphatidylcholine (lysolecithin), lysophosphatidylethanolamine, lyzophosphatidylglycerol, lysophosphatidylinositol, lysophosphatidylglycerol, and lysophosphatidic acid. Further preferable examples are lauryldimethyl aminoacetic acid betaine, lauramidopropyl betaine, lauryl hydroxy sulfobetaine, stearyl betaine, and lysophosphatidylcholine (lysolecithin).

They can be used singly or in combination of two or more.

In the present invention, a blending amount of the dissolution accelerator is, for example 0.01% by mass to 1% by mass and more preferably 0.10% by mass to 0.50% by mass, based on the total mass of the obtained hydrogel.

In the present invention, a blending amount of the dissolution accelerator is, for example 1% by mass to 30% by mass, preferably 5% by mass to 25% by mass, based on the total mass of the obtained dispersion.

[Polyhydric Alcohol]

By blending a polyhydric alcohol in the dispersion of the present invention, a satisfactory gel can be obtained even when a blending amount of the lipid peptide type compound serving as a gelator is reduced.

The polyhydric alcohol used for the dispersion of the present invention is at least one selected from the group consisting of 1,3-butylene glycol, propylene glycol, and glycerin. The polyhydric alcohol is preferably glycerin or 1,3-butanediol, further preferably 1,3-butanediol.

The polyhydric alcohol is at least one of the alcohols mentioned above. These alcohols can be used singly or in combination of two or more.

In the present invention, a blending amount of the polyhydric alcohol is, for example 0.1% by mass to 10% by mass and more preferably 1% by mass to 5% by mass, based on the total mass of the obtained hydrogel.

In the present invention, a blending amount of the polyhydric alcohol is, for example 5% by mass to 30% by mass, preferably 15% by mass to 25% by mass, based on the total mass of the obtained dispersion.

In the present invention, the dispersion containing the lipid peptide type compound, the dissolution accelerator, and the polyhydric alcohol can be suitably used as a thickener for an antifreezing agent.

[Polymer Emulsifier]

The dispersion of the present invention to which a polymer emulsifier is added can give a gel, even when the heated gelator dispersion is stirred during the gel preparation. As the polymer emulsifier, at least one polymer compound selected from the group consisting of a graft polymer compound produced by grafting a hydrophobic moiety to a hydrophilic backbone and a block polymer compound containing a hydrophobic structural unit and a hydrophilic structural unit may be blended in the dispersion of the present invention.

Examples of the graft polymer compound produced by grafting a hydrophobic moiety to a hydrophilic backbone include xanthan gum, alginic acid esters, and cellulose derivatives.

Examples of the block polymer compound containing a hydrophobic structural unit and a hydrophilic structural unit include copolymers of alkyl acrylates-alkyl methacrylates.

As the polymer compound, a compound selected from the group consisting of a carboxymethyl cellulose and an alginic acid ester is preferred, and propylene glycol alginate is particularly preferred.

The polymer emulsifier used in the present invention is at least one selected from the group consisting of graft polymer compounds and block polymer compounds. These polymer compounds can be used singly or in combination of two or more.

In the present invention, a blending amount of the polymer emulsifier is, for example 0.1% by mass to 5% by mass and more preferably 0.2% by mass to 0.5% by mass, based on the total mass of the obtained hydrogel.

As the dispersion of the present invention, the dispersion containing the lipid peptide type compound as a gelator and containing in addition to the dissolution accelerator and the polyhydric alcohol, the polymer emulsifier can be suitably used as a premix for preparing a cosmetic or a quasi-drug, that is, as a premix material for preparing a gel used for a cosmetic or a quasi-drug. In addition, in this dispersion (premix), a heat resistance improver and various known additives as an additive for at least one of a cosmetic and a quasi-drug that are described below can also be blended.

The premix can be produced by: adding a dissolution accelerator and a polyhydric alcohol to a lipid peptide type compound to stir the resultant mixture at room temperature or higher and lower than 100° C., preferably 50° C. to 90° C., and more preferably 60° C. to 90° C., for example 80° C.; and if desired, adding a heat resistance improver and an additive for at least one of a cosmetic and a quasi-drug to the above mixture to stir the resultant mixture.

[Heat Resistance Improver]

As the heat resistance improver used for the dispersion of the present invention, a higher alcohol or a higher fatty acid ester may be added to the dispersion.

Examples of the higher alcohol include saturated and unsaturated higher alcohols as follow: lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol-2-decyltetradecynol, cholesterol, phytosterol, sitosterol, lanosterol, POE cholesterol ether, and monostearyl glycerin ether (batyl alcohol).

Among the higher alcohols above, one selected from the group consisting of $C_{10-20}$ saturated and unsaturated higher alcohols is preferred. Preferred examples are lauryl alcohol, myristyl alcohol, palmityl alcohol, stearyl alcohol, behenyl alcohol, oleyl alcohol, isostearyl alcohol, cholesterol, phytosterol, sitosterol, lanosterol, and monostearyl glycerin ether (batyl alcohol). Further preferred examples are lauryl alcohol, palmityl alcohol, and myristyl alcohol.

Examples of the higher fatty acid ester include saturated and unsaturated higher fatty acid esters as follow: ester oils such as diisobutyl adipate, 2-hexyldecyl adipate, di-2-heptylundecyl adipate, N-alkylglycol monoisostearate, isocetyl isostearate, trimethylolpropane triisostearate, ethylene glycol di-2-ethylhexanoate-cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, N-lauroyl-L-glutamic acid 2-octyl dodecyl ester, and diisostearyl malate; and glyceride oils such as acetoglyceride, glyceride triisooctanoate, glyceride triisostearate, glyceride triisopalmitate, glyceride tri-2-ethylhexanoate, glyceride monostearate, glyceride di-2-heptylundecanoate, and glyceride trimyristate.

Among the higher fatty acid esters, at least one selected from the group consisting of $C_{10-20}$ saturated higher fatty acid esters is preferred. Preferred examples include N-alkylglycol monoisostearate and glyceride monostearate. Further preferred example is glyceride monostearate (glyceryl monostearate).

In the present invention, a blending amount of the heat resistance improver is, for example 0.01% by mass to 0.30% by mass, preferably 0.02% by mass to 0.10% by mass, based on the total mass of the obtained hydrogel.

In the present invention, a blending amount of the heat resistance improver is, for example 0.2% by mass to 1.0% by mass, preferably 0.1% by mass to 0.5% by mass, based on the total mass of the obtained dispersion.

The heat resistance improver used in the present invention is at least one type selected from the above group of fatty acids and these fatty acids may be used individually or in combination of two or more types thereof.

[Other Additives]

In the composition of the premix, if necessary, an additive generally usable as an additive for cosmetics and an additive for quasi-drugs may be blended. Examples of an adding ingredient of a biologically active substance, a functional substance, and the like that are blended in an external preparation for skin such as cosmetics and quasi-drugs include oleaginous bases, moisturizers, touch improvers, surfactants, polymers, thickening/gelators, solvents, propellants, antioxidants, reducing agents, oxidizing agents, sterilizers, antimicrobe agents, bactericides, chelating agents, pH adjusters, acids, alkalis, powder, inorganic salts, ultraviolet absorbers, whitening agents, vitamins and derivatives thereof, agents for hair growth, blood circulation accelerators, stimulants, hormones, anti-wrinkle agents, anti-aging agents, tightening agents, cold sensing agents, warm sensing agents, wound healing promoters, irritation mitigators, analgesics, cell activators, plant/animal/microbe extracts, anti-pruritic agents, corneum releasing/dissolving agents, antiperspirants, refrigerants, astringent agents, enzymes, nucleic acids, perfumes, dyestuffs, colorants, dyes, pigments, antiphlogistic agents, antiinflammatory agents, antiasthmatic agents, anti-chronic obstructive pulmonary disease agents, antiallergic agents, immunomodulators, anti-infectious disease agents, and antifungal agents.

These adding ingredients are exemplified as follows.

Preferred examples of the oleaginous base include: higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diol; aralkyl alcohols and derivatives thereof such as benzyl alcohol; higher fatty acids such as lauric acid, myristic acid, palmitic acid, stearic acid, isostearic acid, behenic acid, undecylenic acid, 12-hydroxystearic acid, palmitoleic acid, oleic acid, linoleic acid, linolenic acid, erucic acid, docosahexaenoic acid, eicosapentaenoic acid, isohexadecanoic acid, anteiso-heneicosanoic acid, long-chain branched fatty acids, dimeric acid, and hydrogenated dimeric acid, and an aluminum salt, a calcium salt, a magnesium salt, a zinc salt, a potassium salt, and a sodium salt of above higher fatty acids that are metal soaps, and an amide of above higher fatty acids that are nitrogen-containing derivatives of above higher fatty acids; hydrocarbons such as liquid paraffin (mineral oil), heavy liquid isoparaffin, light liquid isoparaffin, an α-olefin oligomer, polyisobutene, hydrogenated polyisobutene, polybutene, squalane, squalane derived from olive, squalene, vaseline, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch wax, polyethylene wax, and ethylene-propylene copolymer; vegetable oils and fats such as coconut oil, palm oil, palm kernel oil, safflower oil, olive oil, castor oil, avocado oil, sesame oil, tea seed oil, evening primrose oil, wheat germ oil, macadamia nut oil, hazelnut oil, candlenut oil, rose hip oil, meadowfoam oil, persic oil, tea tree oil, peppermint oil, corn oil, rapeseed oil, sunflower oil, wheat germ oil, linseed oil, cotton seed oil, soybean oil, peanut oil, rice bran oil, cacao butter, shea butter, hydrogenated coconut oil, hydrogenated castor oil, jojoba oil, and hydrogenated jojoba oil; animal oils and fats such as beef tallow, milk fat, horse fat, egg yolk oil, mink oil, and turtle oil; animal waxes such as spermaceti wax, lanolin, and orange roughy oil; lanolin such as liquid lanolin, reduced lanolin, adsorptively purified lanolin, lanolin acetate, acetylated lanolin, hydroxylated lanolin, polyoxyethylene lanolin, lanolin fatty acid, hard lanolin fatty acid, lanolin alcohol, acetylated lanolin alcohol, and an acetic acid (cetyl-lanolyl) ester; phospholipids such as lecithin, phosphatidylcholine, phosphatidyl ethanolamine, phosphatidylserine, phosphatidylglycerol, phosphatidylinositol, sphingophospholipids such as sphingomyelin, phosphatidic acid, and lysolecithin; phospholipid derivatives such as hydrogenated soybean phospholipid, partially hydrogenated soybean phospholipid, hydrogenated egg yolk phospholipid, and partially hydrogenated egg yolk phospholipid; sterols such as cholesterol, dihydrocholesterol, lanosterol, dihydrolanosterol, phytosterol, and cholic acid; sapogenin; saponin; sterol esters such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, acylsarcosine alkyl esters such as isopropyl N-lauroylsarcosinate, cholesteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branched fatty acid cholesteryl, and long-chain α-hydroxy fatty acid cholesteryl; lipid complexes such as phospholipid-cholesterol complex and phospholipid-phytosterol complex; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentananoate, isostearyl neopentanoate, octyldodecyl neodecanoate, oleyl oleate, octyldodecyl oleate, octyldodecyl ricinoleate, lanolin fatty acid octyldodecyl, hexyldecyl dimethyloctanoate, octyldodecyl erucate, hydrogenated castor oil isostearate, ethyl oleate, avocado oil fatty acid ethyl, isopropyl myristate, isopropyl palmitate, octyl palmitate, isopropyl isostearate, lanolin fatty acid isopropyl, diethyl sebacate, diisopropyl sebacate, dioctyl sebacate, diisopropyl adipate, dibutyloctyl sebacate, diisobutyl adipate, dioctyl succinate, and triethyl citrate; oxy acid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, glyceryl tri(caprylate/caprinate), glyceryl tri(caprylate/caprinate/myristate/stearate), hydrogenated rosin glyceride (hydrogenated ester gum), rosin triglyceride (ester gum), glyceryl behenate/eicosanedienoate, trimethylolpropane trioctanoate, trimethylolpropane triisostearate, neopentyl glycol dioctanoate, neopentyl glycol dicaprinate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), diglyceryl oligoester of (hexyldecanoic acid/sebacic acid), glycol distearate (ethylene glycol distearate), 3-methyl-1,5-pentanediol dineopentanoate, and 2,4-diethyl-1,5-pentanediol dineopentanoate; derivatives of dimer acids or dimer diols such as diisopropyl dimer-dilinoleate, diisostearyl dimer-dilinoleate, di(isostearyl/phytosteryl) dimer-dilinoleate, (phytosteryl/behenyl) dimer-dilinoleate, (phytosteryl/isostearyl/cetyl/stearyl/behenyl) dimer-dilinoleate, dimer-dilinoleyl dimer-dilinoleate, dimer-dilinoleyl diisostearate, dimer-dilinoleyl-hydrogenated rosin condensate, hydrogenated castor oil dimer-dilinoleate, and hydroxyalkyl dimer-dilinoleyl ether; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamidemethyl MEA); silicones such as dimethicone (dimethylpolysiloxane), dimethicone having high degree of polymerization (dimethyl polysiloxane having high degree of polymerization), cyclomethicone (cyclic dimethylsiloxane, decamethylcyclopentasiloxane), phenyl trimethicone, diphenyl dimethicone, phenyl dimethicone, stearoxypropyldimethylamine, a (aminoethylaminopropyl methicone/dimethicone) copolymer, dimethiconol, a dimethiconol crosspolymer, silicone resin, silicone rubber, amino-modified silicone such as aminopropyl dimethicone and amodimethicone, cation-modified silicone, polyether-modified silicone such as dimethicone copolyol, polyglycerin-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified and polyether-modified silicone, amino-modified and polyether-modified silicone, alkyl-modified and polyether-modified silicone, and polysiloxane-oxyalkylene copolymer; and fluorine-based oil solutions such as perfluorodecane, perfluorooctane, and perfluoropolyether.

Preferred examples of the moisturizer and the touch improver include: polyols such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymer and polymers of these polyols; glycol alkyl ethers such as diethylene glycol monoethyl ether (ethoxy diglycol), ethylene glycol monoethyl ether, ethylene glycol monobutyl ether, and diethylene glycol dibutyl ether; water soluble esters such as polyglyceryl-10 (eicosanedienoate/tetradecanedienoate) and polyglyceryl-10 tetradecanedienoate; sugar alcohols such as sorbitol, xylitol, erythritol, mannitol, and maltitol; saccharides such as glucose, fructose, galactose, mannose, threose, xylose, arabinose, fucose, ribose, deoxyribose, maltose, trehalose, lactose, raffinose, gluconic acid, glucuronic acid, cyclodextrins (α-cyclodextrin, β-cyclodextrin, γ-cyclodextrin, and modified cyclodextrin such as maltosylated cyclodextrin and hydroxyalkylated cyclodextrin), β-glucan, chitin, chitosan, heparin and derivatives thereof, pectin, arabinogalactan, dextrin, dextran, glycogen, ethyl glucoside, and polymers or copolymers of glucosylmethyl methacrylate, and derivatives of these saccharides; hyaluronic acid and sodium hyaluronate; sodium chondroitin sulfate; mucoitinsulfuric acid, charonin sulfate, keratosulfate, and dermatan sulfate; *Tremella fuciformis* extracts and *Tremella fuciformis* polysaccharides; fucoidan; *tuberosa* polysaccharides or natural polysaccharides; organic acids such as citric acid, tartaric acid, and lactic acid, and salts thereof; urea and derivatives thereof; 2-pyrrolidone-5-carboxylic acid and salts thereof such as a sodium salt; amino acids such as betaine (trimethylglycine), proline, hydroxyproline, alginine, lysine, serine, glycine, alanine, phenylalanine, tyrosine, β-alanine, threonine, glutamic acid, glutamine, asparagine, aspartic acid, cysteine, cysteine, methionine, leucine, isoleucine, valine, tryptophan, histidine, and taurine, and salts of these amino acids; protein peptides such as collagen, fish-derived collagen, atelocollagen, gelatin, elastin, collagen decomposed peptide, hydrolyzed collagen, hydroxypropylammonium chloride-hydrolyzed collagen, elastin decomposed peptide, keratin decomposed peptide, hydrolyzed keratin, conchiolin decomposed peptide, hydrolyzed conchiolin, silk protein decomposed peptide, hydrolyzed silk, lauroyl-hydrolyzed silk sodium, soybean protein decomposed peptide, wheat protein decomposed peptide, hydrolyzed wheat protein, casein decomposed peptide, and acylated peptide, and derivatives of these protein peptides; acylated peptides such as palmitoyl oligopeptide, palmitoyl pentapeptide, and palmitoyl tetrapeptide; silylated peptides; a culture solution for lactic acid bacterium, yeast extract, eggshell membrane protein, cow submaxillary gland mucin, hypotaurine, sesame lignan glycoside, glutathione, albumin, and milk serum; choline chloride and phosphorylcholine; animal/plant extracted components such as placenta extract, elastin, collagen, aloe extract, *hamamelis* water, sponge cucumber water, *chamomilla* extract, licorice extract, comfrey extract, silk extract, chestnut rose extract, yarrow extract, *eucalyptus* extract, and melilot extract, ceramides such as natural ceramide (type 1, 2, 3, 4, 5, 6), hydroxyceramide, pseudo-ceramide, sphingoglycolipid, and extracts containing ceramide or ceramide saccharide.

Preferred examples of the surfactant include anionic surfactants, nonionic surfactants, cationic surfactants, amphoteric surfactants, and polymer surfactants. Preferred examples of the surfactant are as follows. Preferred examples of the anionic surfactant include, for example, salts of fatty acids such as potassium laurate and potassium myristate; alkyl sulfates such as sodium lauryl sulfate, triethanolamine lauryl sulfate, and ammonium lauryl sulfate; polyoxyethylene alkyl sulfates such as sodium laureth sulfate and triethanolamine laureth sulfate; salts of acyl-N-methylamino acids such as sodium cocoylmethyl taurate, potassium cocoylmethyl taurate, sodium lauroylmethyl taurate, sodium myristoylmethyl taurate, sodium lauroylmethyl alaninate, sodium lauroyl sarcosinate, triethanolamine lauroyl sarcosinate, and sodium methylalanine lauroyl glutamate; salts of acylamino acids such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroylmonoethanolamide succinate; fatty acid alkanolamide ether carboxylates; acyl lactates; polyoxyethylene aliphatic amine sulfates; fatty acid alkanolamide sulfates; fatty acid glyceride sulfates such as glycerin hydrogenated coconut oil fatty acid sulfate sodium salt; alkylbenzene polyoxyethylene sulfates; olefin sulfonates such as sodium α-olefin sulfonate; alkyl sulfosuccinates such as disodium lauryl sulfosuccinate and sodium dioctylsulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkyl benzene sulfonates such as sodium tetradecylbenzenesulfonate and triethanolamine tetradecylbenzenesulfonate; alkylnaphthalenesulfonates; alkanesulfonates; methyl ester salts of α-sulfo fatty acids; acylisethionic acid salts; alkyl glycidyl ether sulfonates; alkyl sulfo acetates; alkyl ether phosphates such as sodium laureth phosphate, sodium dilaureth phosphate, sodium trilaureth phosphate, and sodium monooleth phosphate; alkyl phosphates such as potassium lauryl phosphate; sodium caseinate; alkyl aryl ether phosphates; fatty amide ether phosphates; phospholipids such as phosphatidylglycerol, phosphatidylinositol, and phosphatidic acid; silicone-based anion surfactants such as carboxylic acid-modified silicone, phosphoric acid-modified silicone, and sulfuric acid-modified silicone. Preferred examples of the nonionic surfactant include, for example, polyoxyethylene alkyl ethers having various numbers of added molecules of polyoxyethylene such as laureth (polyoxyethylene lauryl ether) group, ceteth (polyoxyethylene cetyl ether) group, steareth (polyoxyethylene stearyl ether) group, beheneth (polyoxyethylene behenyl ether) group, isosteareth (polyoxyethylene isostearyl ether) group, and octyldodeceth (polyoxyethylene octyldodecyl ether) group; polyoxyethylene alkyl phenyl ethers; derivatives of castor oil and hydrogenated castor oil such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate-monoisostearate-diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether, polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glycerin coconut oil fatty acid ester, glycerin mono cottonseed oil fatty acid ester, glyceryl monoerucate, glyceryl sesquioleate, glycerin ester of α,α'-oleic acid-pyroglutamic acid, and glyceryl monostearate malic acid; polyglycerin fatty acid esters such as polyglyceryl-2,3,4,5,6,8, or 10 stearate, polyglyceryl-2 tristearate, polyglyceryl-10 decastearate, polyglyceryl-2,3,4,5,6,8, or 10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2,3,4,5,6,8, or 10 oleate, polyglyceryl-6 dioleate, polyglyceryl-2 trioleate, and polyglyceryl-10 decaoleate; ethylene glycol mono fatty acid ester such as ethylene glycol monostearate; propylene glycol mono fatty acid ester such as propylene glycol monostearate; pentaerythritol fatty acid partial ester; sorbitol fatty acid partial ester; maltitol fatty acid partial ester; maltitol ether; sorbitan fatty acid ester such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; saccharide derivative partial esters such as sucrose fatty acid ester, methylglucoside fatty acid ester, and trehalose undecylate; alkyl glucoside such as caprylyl glucoside; alkylpolyglucoside; lanolin alcohol; reduced lanolin; polyoxyethylene fatty acid mono- and di-ester such as polyoxyethylene distearate, polyoxyethylene diisostearate, polyoxyethylene monooleate, and polyoxyethylene dioleate; polyoxyethylene propylene glycol fatty acid ester; polyoxyethylene glycerin fatty acid ester such as polyoxyethylene monooleate such as polyoxyethylene glycerin monostearate, polyoxyethylene glycerin monoisostearate, and polyoxyethylene glycerin triisostearate; polyoxyethylene sorbitan fatty acid ester such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid ester such as polyoxyethylene sorbitol monolaurate, polyoxyethylene sorbitol monooleate, polyoxyethylene sorbitol pentaoleate, and polyoxyethylene sorbitol monostearate; polyoxyethylene methylglucoside fatty acid ester; polyoxyethylene alkyl ether fatty acid ester; polyoxyethylene animal and vegetable oils and fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ether; polyoxyethylene alkylamine; tetrapolyoxyethylene/tetrapolyoxypropylene-ethylenediamine condensates; nature-originated surfactants such as saponin and sophorolipid; polyoxyethylene fatty acid amide; fatty acid alkanolamides such as coconut oil fatty acid monoethanolamide (cocamide MEA), coconut oil fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (paltamide MEA), palmitic acid diethanolamide (paltamide DEA), and coconut oil fatty acid methylethanolamide (cocamide methyl MEA); alkyldimethylamine oxides such as lauramine oxide, cocamine oxide, stearamine oxide, and behenamine oxide; alkylethoxydimethylamine oxides; polyoxyethylene alkyl mercaptans; polyether-modified silicones such as dimethicone copolyol; and silicone-based nonionic surfactants such as polysiloxane-oxyalkylene copolymers, polyglycerin-modified silicone, and saccharide-modified silicone. Preferred examples of the cationic surfactant include: alkyltrimethylammonium chlorides such as behentrimonium chloride, steartrimonium chloride, cetrimonium chloride, and lauryltrimonium chloride; alkyltrimethylammonium bromides such as steartrimonium bromide; dialkyldimethylammonium chlorides such as disteardimonium chloride and dicocodimonium chloride; fatty acid amido amines such as stearamidopropyl dimethylamine and stearamidoethyl diethylamine, and salts thereof; alkyletheramines such as stearoxypropyl dimethylamine, and salts or quaternary salts thereof; fatty acid amide-type quaternary ammonium salts such as long-chain fatty acid (12 to 31) aminopropylethyldimethylammonium ethyl sulfate and lanolin fatty acid aminopropylethyldimethylammonium ethyl sulfate; polyoxyethylene alkylamines and salts or quaternary salts thereof; alkylamine salts; fatty acid amide guanidium salt; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone-based cationic surfactants such as amino-modified silicone such as aminopropyl dimethicone and amodimethicone, cation-modified silicone, cation-modified and polyether-modified silicone, and amino-modified and polyether-modified silicone. Preferred examples of the amphoteric surfactant include N-alkyl-N,N-dimethyl amino acid betaines such as lauryl betaine (lauryldimethyl aminoacetic acid betaine); fatty acid amide alkyl-N,N-dimethyl amino acid betaines such as cocamidopropyl betaine and lauramidopropyl betaine; imidazoline-type betaines such as sodium cocoamphoacetate and sodium lauroamphoacetate; alkylsulfo betaines such as alkyl dimethyl taurine; sulfuric acid-type betaines such as alkyl dimethyl amino ethanol sulfuric acid ester; phosphoric acid-type betaines such as alkyl dimethyl amino ethanol phosphoric acid ester; phospholipids such as sphingophospholipids such as phosphatidylcholine, phosphatidyl ethanolamine, phosphatidylserine, and sphingomyelin, lysolecithin, hydrogenated soybean phospholipid, partially hydrogenated soybean phospholipid, hydrogenated egg yolk phospholipid, partially hydrogenated egg yolk phospholipid, and lecithin hydroxide; and silicone-based amphoteric surfactants. Preferred examples of the polymer surfactant include polyvinyl alcohols, sodium alginate, starch derivatives, tragacanth gum, copolymers of alkyl acrylates or alkyl methacrylates, and various silicone-based surfactants.

Preferred examples of the polymer, the thickener, and the gelator include: guar gum; locust bean gum; quince seed; carrageenan; galactan; gum arabic; tara gum; tamarind; furcellaran; karaya gum; sunset hibiscus; cara gum; tragacanth gum; pectin; pectic acid and salts such as a sodium salt thereof; alginic acid and salts such as a sodium salt thereof; mannan; starches of rice, corn, potato, and wheat; xanthan gum; dextran; succinoglucan; curdlan; hyaluronic acid and salts thereof; xanthan gum; pullulan, gellan gum; chitin; chitosan; agar, brown alga extract; chondroitin sulfate salt; casein; collagen; gelatin; albumin; celluloses and derivatives thereof such as methyl cellulose, ethyl cellulose, hydroxyethyl cellulose, hydroxypropyl cellulose, hydroxypropylmethyl cellulose, carboxymethyl cellulose and salts such as a sodium salt thereof, methylhydroxypropyl cellulose, sodium cellulose sulfate, dialkyldimethyl ammonium sulfate cellulose, crystalline cellulose, and powdered cellulose; starch polymers such as soluble starch, carboxymethyl starch, methylhydroxypropyl starch, and methyl starch; starch derivatives such as starch hydroxypropyltrimonium chloride, and aluminum corn starch octenylsuccinate; alginic acid derivatives such as sodium alginate and propylene glycol alginate ester; polyvinylpyrrolidone (PVP); polyvinylalcohol (PVA); vinylpyrrolidone-vinylalcohol copolymers; polyvinyl methyl ether; polyethylene glycol; polypropylene glycol; polyoxyethylene-polyoxypropylene copolymers; amphoteric methacrylate ester copolymers such as (methacryloyloxyethylcarboxybetaine/alkyl methacrylate) copolymer and (acrylates/stearyl acrylate/ethylamine oxide methacrylate) copolymer, (dimethicone/vinyldimethicone) cross polymers; (alkyl acrylate/diacetoneacrylamide) copolymer and AMP-(alkyl acrylate/diacetoneacrylamide) copolymer; polyvinyl acetate partially saponified products; maleic acid polymers; vinylpyrrolidone-dialkylaminoalkyl methacrylate copolymers; acrylic resin alkanolamines; polyesters and water-dispersible polyesters; polyacrylamides; copolymers of polyacrylate ester such as ethyl polyacrylate; carboxyvinyl polymers; polyacrylic acid and salts such as a sodium salt thereof; copolymers of acrylate esters-methacrylate esters; copolymers of alkyl acrylates-alkyl methacrylates; cationized celluloses such as polyquaternium-10; diallyldimethylammonium chloride-acrylamide copolymers such as polyquaternium-7; acrylic acid-diallyldimethylammonium chloride copolymers such as polyquaternium-22; acrylic acid-diallyldimethylammonium chloride-acrylamide copolymers such as polyquaternium-39; copolymers of acrylate esters-cationized methacrylate esters; copolymers of alkyl acrylates-cationized alkyl methacrylates; copolymers of acrylamides-cationized methacrylamides; acrylic acid-methyl acrylate-methacrylamidepropyltrimethylammonium chloride copolymers such as polyquaternium-47; methacryloyl chloride choline ester polymers; cationized polysaccharides such as cationized oligosaccharides, cationized dextran; guar hydroxypropyltrimonium chloride; polyethyleneimines; cation polymers; polymers of 2-methacryloyloxyethyl phosphorylcholine such as polyquaternium-51, and copolymers thereof with a butyl methacrylate-copolymer; polymer emulsions such as an acrylic resin emulsion, an ethyl polyacrylate emulsion, a polyacrylalkyl ester emulsion, a polyvinyl acetate resin emulsion, natural rubber latex, and synthetic latex; nitrocelluloses; polyurethanes and various copolymers; various silicones; various silicone-based copolymers such as an acryl-silicone graft copolymer; various fluorine-based polymers; 12-hydroxystearic acid and salts thereof; dextrin fatty acid esters such as dextrin palmitate and dextrin myristate; silicic anhydride and fumed silica (ultrafine particle silicic anhydride); magnesium aluminum silicate and magnesium sodium silicate; metal soaps; dialkylphosphoric acid metal salts; bentonite; hectorite; organic modified clay minerals; saccharose fatty acid esters; and fructo-oligosaccharide fatty acid esters. Among the above examples, preferred are celluloses and derivatives thereof, alginic acid and salts thereof, polyvinyl alcohols, hyaluronic acid and salts thereof, and collagen.

Preferred examples of the solvent and the propellant include: lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyl diol; glycol ethers such as diethylene glycol monoethyl ether (ethoxy diglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol; benzyloxyethanol; propylene carbonate; dialkyl carbonate; acetone; ethyl acetate; N-methylpyrrolidone; toluene; and propellants such as fluorocarbon, freon gas for the next generation, LPG dimethyl ether, and carbon dioxide.

Preferred examples of the antioxidant include: tocopherol derivatives such as tocopherol (vitamin E) and tocopherol acetate; BHT and BHA; gallic acid derivatives such as propyl gallate; at least one of vitamin C (ascorbic acid) and derivative thereof; erythorbic acid and derivatives thereof; sulfites such as sodium sulfite; hydrogensulfites such as sodium hydrogensulfite; thiosulfates such as sodium thiosulfate; metabisulfites; thiotaurine and hypotaurine; thioglycerol, thiourea, and thioglycolic acid; and cysteine hydrochloride.

Preferred examples of the reducing agent include thioglycolic acid, cysteine, and cysteamine.

Preferred examples of the oxidizing agent include hydrogen peroxide water, ammonium persulfate, sodium bromate, and percarbonic acid.

Preferred examples of the sterilizer, the antimicrobe agent, and the bactericide include hydroxybenzoic acid and salts thereof or esters thereof such as methylparaben, ethylparaben, propylparaben, and butylparaben; salicylic acid; sodium benzoate; phenoxy ethanol; isothiazolinone derivatives such as methyl-chloro-isothiazolinone and methyl-isothiazolinone; imidazolinium urea; dehydroacetic acid and salts thereof; phenols; halogenated bisphenols such as triclosan; acid amides; quaternary ammonium salts; trichlorocarbanilide; zinc pyrithione; benzalkonium chloride; benzethonium chloride; sorbic acid, chlorohexidine; chlorohexidine glucanate; halocarban; hexachlorophene; hinokitiol; phenols other than the above phenols such as phenol, isopropylphenol, cresol, thymol, p-chlorophenol, phenylphenol, and sodium phenylphenate; phenylethyl alcohol; photosensitive elements; antibacterial zeolite; and silver ion.

Preferred examples of the chelating agent include: edetates (ethylenediaminetetraacetates) such as EDTA, EDTA2Na, EDTA3Na, and EDTA4Na; hydroxyethylethylenediaminetriacetates such as HEDTA3Na; pentetates (diethylenetriaminepentaacetates); phosphonic acids such as phytic acid and etidronic acid, and salts such as a sodium salt thereof; sodium oxalate; polyamino acids such as polyaspartic acid and polyglutamic acid; sodium polyphosphate, sodium metaphosphate, and phosphoric acid; sodium citrate and citric acid; alanine; dihydroxyethylglycine; gluconic acid; ascorbic acid; succinic acid; and tartaric acid.

Preferred examples of the pH adjuster, the acid, and the alkali include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propandiol, 2-amino-2-hydroxymethyl-1,3-propanediol, arginine, sodium hydroxide, potassium hydroxide, ammonia water, guanidine carbonate, and ammonium carbonate.

Preferred examples of the powder include: inorganic powder having various sizes and shapes such as mica, talc, kaolin, sericite, biotite, montmorillonite, kaolinite, isinglass, muscovite, phlogopite, synthetic isinglass, lepidolite, vermiculite, magnesium carbonate, calcium carbonate, aluminum silicate, barium silicate, potassium silicate, magnesium silicate, strontium silicate, a metal salt of tangstic acid, magnesium, zeolite, barium sulfate, baked calcium sulfate, calcium phosphate, fluoroapatite, hydroxyapatite, ceramic powder, bentonite, smectite, clay, mud, metal soap (for example, zinc myristate, calcium palmitate, aluminum stearate), calcium carbonate, red iron oxide, yellow iron oxide, black iron oxide, ultramarine, Prussian blue, carbon black, titanium oxide, fine particle or ultrafine particle titanium oxide, zinc oxide, fine particle or ultrafine particle zinc oxide, alumina, silica, fumed silica (ultrafine particle silicic anhydride), mica titanium, fish scale guanine, boron nitride, a photochromic pigment, synthetic fluorophlogopite, fine particle compound powder, gold, and aluminum; inorganic powder that is powder hydrophobized or hydrophilized by subjecting the above inorganic powder to a treatment using various surface treating agent such as silicone such as hydrogen silicone and cyclic hydrogen silicone, another silane, or a titanium coupling agent; organic powder having various sizes and shapes such as starch, cellulose, nylon powder, polyethylene powder, poly(methyl methacrylate) powder, polystyrene powder, powder of a copolymer resin of styrene and acrylic acid, polyester powder, benzoguanamine resin powder, powder in which polyethylene terephthalate and poly(methyl methacrylate) are layered, powder in which polyethylene terephthalate, aluminum, and epoxy are layered, urethane powder, silicone powder, and Teflon (registered trademark) powder, and surface treated powder; and organic-inorganic compound powder.

Preferred examples of the inorganic salt include: sodium chloride-containing salts such as a salt, a crude salt, a rock salt, a sea salt, and a natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as monosodium dihydrogen phosphate, disodium hydrogen phosphate, and trisodium phosphate, potassium phosphates, calcium phosphates, and magnesium phosphates.

Preferred examples of the ultraviolet absorber include: benzoic acid-based ultraviolet absorbers such as p-aminobenzoic acid, p-aminobenzoic acid monoglycerin ester, N,N-dipropoxy-p-aminobenzoic acid ethyl ester, N,N-diethoxy-p-aminobenzoic acid ethyl ester, N,N-dimethyl-p-aminobenzoic acid ethyl ester, N,N-dimethyl-p-aminobenzoic acid butyl ester, and N,N-dimethyl-p-aminobenzoic acid ethyl ester; anthranilic acid-based ultraviolet absorbers such as homomenthyl-N-acetylanthranilate; salicylic acid-based ultraviolet absorbers such as salicylic acid and sodium salt thereof, amyl salicylate, menthyl salicylate, homomenthyl salicylate, octyl salicylate, phenyl salicylate, benzyl salicylate, and p-isopropanolphenyl salicylate; cinnamic acid-based ultraviolet absorbers such as octyl cinnamate, ethyl 4-isopropyl-cinnamate, methyl 2,5-diisopropyl-cinnamate, ethyl 2,4-diisopropy-cinnamate, methyl 2,4-diisopropyl-cinnamate, propyl p-methoxycinnamate, isopropyl p-methoxycinnamate, isoamyl p-methoxycinnamate, 2-ethylhexyl p-methoxycinnamate (octyl p-methoxycinnamate), 2-ethylethyl p-methoxycinnamate (cinoxate), cyclohexyl p-methoxycinnamate, ethyl $\alpha$-cyano-$\beta$-phenyl-cinnamate, 2-ethylhexyl $\alpha$-cyano-$\beta$-phenylcinnamate (octocrylene), glyceryl mono-2-ethylhexanoyl-di-p-methoxycinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methyl benzophenone, 2-hydroxy-4-methoxybenzophenone 5-sulfonate, 4-phenylbenzophenone, 2-ethylhexyl-4'-phenyl-benzophenone 2-carboxylate, 2-hydroxy-4-n-octoxybenzophenone, and 4-hydroxy-3-carboxybenzophenon; 3-(4'-methylbenzylidene)-d,l-camphor; 3-benzylidene-d,l-camphor; 2-phenyl-5-methylbenzoxazole; 2,2'-hydroxy-5-methylphenyl-benzotriazole; 2-(2'-hydroxy-5'-t-octylphenyl)

benzotriazole; 2-(2'-hydroxy-5'-methylphenyl) benzotriazole; dibenzalazine; dianisoylmethane; 5-(3,3-dimethyl-2-norbornylidene)-3-pentan-2-one; dibenzoylmethane derivatives such as 4-t-butylmethoxy-dibenzoylmethane; octyltriazone; urocanic acid derivatives such as urocanic acid and ethyl urocanate; 2-(2'-hydroxy-5'-methylphenyl)benzotriazole; 1-(3,4-dimethoxyphenyl)-4, 4-dimethyl-1,3-pentanedione; hydantoin derivatives such as 2-ethylhexyl dimethoxybenzylidene dioxoimidazolidine propionate; phenylbenzimidazole sulfonic acid; terephthalylidene dicamphor sulfonic acid; drometrizole trisiloxane; methyl anthranilate; rutin and derivatives thereof; and orizanol and derivatives thereof.

Preferred examples of the whitening agent include: hydroquinone glucoside such as arbutin and α-arbutin, and esters thereof; ascorbic acid derivatives such as ascorbic acid, ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbic acid alkyl ether such as ascorbic acid ethyl ether, ascorbic acid glucoside such as ascorbic acid-2-glucoside and fatty acid ester thereof, ascorbic acid sulfate ester, and ascorbyl tocopheryl phosphate; kojic acid; ellagic acid, tranexamic acid and derivatives thereof; ferulic acid and derivatives thereof; placenta extract; glutathione; orizanol; butyl resorcinol; and plant extracts such as oil-soluble *chamomilla* extract, oil-soluble licorice extract, Seikaryu extract, and *Saxifraga sarementosa* extract.

Preferred examples of the vitamin group and derivatives thereof include: vitamin A group such as retinol, retinol acetate, and retinol palmitate; vitamin B group such as thiamine hydrochloride salt, thiamine sulfate salt, riboflavin, riboflavin acetate, pyridoxine hydrochloride, pyridoxine dioctarioate, pyridoxine dipalmitate, flavin adenine dinucleotide, cyanocobalamin, folic acids, nicotinic acid group such as nicotinic acid amide and benzyl nicotinate, and cholines; vitamin C group such as ascorbic acid and salts such as a sodium salt thereof; vitamin D; vitamin E group such as α, β, γ, δ-tocopherol; other vitamins such as pantothenic acid and biotin; ascorbic acid derivatives such as ascorbic acid phosphate ester salts such as ascorbic acid phosphate sodium salt and ascorbic acid phosphate magnesium salt, ascorbic acid fatty acid esters such as ascorbic acid tetraisopalmitate ester, ascorbyl stearate, ascorbyl palmitate, and ascorbyl dipalmitate, ascorbic acid alkyl ether such as ascorbic acid ethyl ether, ascorbic acid glucoside such as ascorbic acid-2-glucoside and fatty acid ester thereof, and ascorbyl tocopheryl phosphate; vitamin derivatives such as tocopherol derivatives such as tocopherol nicotinate, tocopherol acetate, tocopherol linoleate, tocopherol ferulate, and tocopherol phosphate; tocotrienol; and various vitamin derivatives.

Preferred examples of the agent for hair growth, the blood circulation accelerator, and the stimulant include: plant extracts/tinctures such as *Swertia japonica* extract, *capsicum* tincture, *Zingiber officinale* ROSC tincture, *Zingiber officinale* ROSC extract, and cantharides tincture; capsaicin; nonylic acid vanillylamide; zingerone; ichthammol; tannic acid; borneol; cyclandelate; cinnarizine; tolazoline; acetylcholine; verapamil; cepharanthine; γ-oryzanol; vitamin E and derivatives thereof such as tocopherol nicotinate and tocopherol acetate; γ-oryzanol; nicotinic acid and derivatives thereof such as nicotinic amide, benzyl nicotinate, inositol hexanicotinate, and nicotinic alcohol; allantoin; a photosensitive element 301; a photosensitive element 401; capronium chloride; pentadecanoic acid monoglyceride; flavanonol derivatives; stigmasterol or stigmastanol and glucoside thereof; and minoxidil.

Preferred examples of the hormones include estradiol, estrone, ethinylestradiol, cortisone, hydrocortisone, and prednisone. Examples of the anti-wrinkle agent, the anti-aging agent, the tightening agent, the cold sensing agent, the warm sensing agent, the wound healing promoter, the irritation mitigator, the analgesic, and the cell activator as other medical agents include: retinols, retinoic acids, and tocopheryl retinoate; lactic acid, glycolic acid, gluconic acid, fruit acid, salicylic acid, and glucoside and ester compounds thereof; α- or β-hydroxy acids and derivatives thereof such as hydroxycapric acid, long-chain α-hydroxy fatty acids, and long-chain α-hydroxy fatty acid cholesteryl esters; γ-amino butyric acid and γ-amino-β-hydroxy butyric acid; carnitine; carnosine; creatine; ceramides and sphingosines; caffeine and xanthin, and derivatives thereof; antioxidants/active oxygen eliminating agents such as coenzyme Q10, carotene, lycopene, astaxanthin, lutein, α-lipoic acid, platinum nanocolloid, and fullerenes; catechins; flavones such as quercetin; isoflavones; gallic acid and ester saccharide derivatives thereof; polyphenols such as tannin, sesamin, protoanthocyanidin, chlorogenic acid, and apple polyphenols; rutin and derivatives thereof such as glucoside thereof; hesperidin and derivatives thereof such as glucoside thereof; lignan glucoside; substances related to licorice extract such as glabridin, glabrene, liquiritin, and isoliquiritin; lactoferrin; shogaol and gingerol; perfumery material such as menthol and cedrol, and derivatives thereof; capsaicin and vanillin, and derivatives thereof; insect repellents such as diethyltoluamide; complexes of biologically active substances and cyclodextrins.

Examples of the plant/animal/microbe extracts include extracts such as iris extract, *Angelica keiskei* extract, hiba arborvitae extract, asparagus extract, avocado extract, *Hydrangea serrata* extract, almond extract, althea extract, *arnica* extract, aloe extract, apricot extract, apricot kernel extract, *Gingko biloba* extract, *Artemisia capillaris* flower extract, fennel fruit extract, turmeric root extract, oolong tea extract, bearberry leaf extract, *Rosa multiflora* extract, *Echinacea angustifolia* leaf extract, *isodon japonicus* extract, *Scutellaria baicalensis* root extract, phellodendron bark extract, coptis rhizome extract, *Hordeum vulgare* seed extract, *panax ginseng* extract, *Hypericum erectum* extract, *Lamium album* extract, *Ononis spinosa* extract, *Nasturtium officinale* extract, orange extract, dried sea water, sea weed extract, Japanese persimmon leaf extract, *Pyracantha fortuneana* extract, hydrolyzed elastin, hydrolyzed wheat flour, hydrolyzed silk, *pueraria* root extract, Chamomile extract, oil-soluble Chamomile extract, carrot extract, *Artemisia capillaris* flower extract, wild oat extract, karkade extract, licorice extract, oil-soluble licorice extract, kiwi fruit extract, kiou extract, *Auricularia auricula-judae* extract, cinchona bark extract, cucumber extract, *paulownia* leaf extract, guanosine, guava extract, *sophora* root extract, *Gardenia florida* extract, *Sasa veitchii* extract, *Sophora angustifolia* extract, walnut extract, Japanese chestnut extract, grapefruit extract, *clematis* extract, black rice extract, brown sugar extracted substance, black vinegar, *chlorella* extract, *Morus alba* root extract, *Gentiana lutea* extract, geranium herb extract, black tea extract, yeast extract, *magnolia* bark extract, coffee extract, burdock extract, rice extract, fermented rice extract, fermented rice bran extract, rice germ oil, comfrey extract, collagen, *Vaccinium vitis-idaea* extract, Asiasarum root extract, bupleurum root extract, umbilical extract, saffron extract, *Salvia officinalis* extract, *Saponaria officinalis* extract, *Sasa* bamboo grass extract, *Crataegus cuneata* fruit extract, *Bombyx mori* excrementum extract, *Zanthoxylum piperitum* extract, shiitake extract, Rehmannia root extract, *Lithospermum erythrorhizone* root extract, *Perilla frutescens* extract, *Tilia cordata* flower extract, *Filipendula multijuga* extract, Jatoba extract, *Paeonia albiflora* extract, *Zingiber officinale* ROC extract, *Acorus calamus* root extract, *Betula alba* extract, *Tremella fusciformis* extract, *Equisetum arvense* extract, *Stevia rebaudiana* extract, *Stevia rebaudiana* fermentation product, Seikaryu extract, *Hedera helix* L. extract, *Crataegus oxyacantha* extract, *Sambucus nigra* extract, *Achillea millefolium* extract, *Mentha piperita* leaf extract, sage extract, *Malva sylvestris* extract, *Cnidium officinale* root extract, *Swertia japonica* extract, mulberry bark extract, rhuharb extract, soybean extract, zizyphi fructus extract, thyme extract, dandelion extract, Lichenes extract, tea extract, *Eugenia caryophyllus* flower extract, *Imperata cylindrica* extract, *Aurantii nobilis* pericarpium extract, tea tree oil, Tencha extract, red pepper extract, *angelica* root extract, *Calendula officinalis* extract, *Persicae semen* extract, *Citrus aurantium* peel extract, *Houttuynia cordata* extract, tomato extract, natto extract, *ginseng* extract, garlic extract, *Rosa canina* fruit extract, hibiscus extract, Ophiopogon tuber extract, *Nelumbo nucifera* extract, parsley extract, birch extract, honey, *hamamelis* extract, *Parietaria officinalis* extract, *Isodonis japonicus* extract, bisabolol, *Chamaecyparis obtusa* extract, *Lactobacillus bifidus* extract, *Eriobotrya japonica* extract, coltsfoot flower extract, *Petasites japonicus* extract, *Poria cocos* extract, butcher's broom extract, grape extract, grape seed extract, propolis extract, *Luffa cylindrica* fruit extract, safflower flower extract, peppermint extract, *Tilia miqueliana* extract, *Paeonia suffruticosa* root extract, hops extract, *Rosa rugosa* flower extract, pine cone extract, horse chestnut extract, Japanese skunk cabbage extract, *Sapindus mukurossi* peel extract, melissa extract, *Cladosiphon okamuranus* extract, peach extract, *Centaurea cyanus* flower extract, *eucalyptus* extract, *Saxifraga sarementosa* extract, *Citrus junos* extract, lily extract, *coix* seed extract, *Artemisia princeps* extract, lavender extract, green tea extract, eggshell membrane extract, apple extract, rooibos tea extract, lychee extract, lettuce extract, lemon extract, *Forsythiae fructus* extract, *Astragalus sinicus* extract, rose extract, rosemary extract, Roman chamomile extract, royal jelly extract, and *Sanguisorba officinalis* extract.

Examples of the antipruritic agent include diphenhydramine hydrochloride, chlorpheniramine maleate, camphor, and a substance-P inhibitor.

Examples of the corneum releasing/dissolving agent include salicylic acid, sulfur, resorcin, selenium sulfide, and pyridoxine.

Examples of the antiperspirant include chlorohydroxyaluminum, aluminum chloride, zinc oxide, and zinc p-phenolsulfonate.

Examples of the refrigerant include menthol and methyl salicylate.

Examples of the astringent agent include citric acid, tartaric acid, lactic acid, aluminum potassium sulfate, and tannic acid.

Examples of the enzyme include superoxide dismutase, catalase, lysozyme chloride, lipase, papain, pancreatin, and protease.

Preferred examples of the nucleic acids include ribonucleic acids and salts thereof, deoxyribo nucleic acids and salts thereof, and adenosine triphosphate disodium.

Preferred examples of the perfume include synthetic perfumes, natural perfumes, and various compound perfumes such as acetyl cedrene, amylcinnamaldehyde, allyamyl glycolate, β-ionone, Iso E Super, isobutyl quinoline, iris oil, irone, indole, ylang ylang oil, undecanal, undecenal, γ-undecalactone, estragole, eugenol, oakmoss, Opopanax resinoid, orange oil, eugenol, aurantiol, galaxolide, carvacrol, l-carvone, camphor, canon, carrot seed oil, clove oil, geraniol, geranyl nitrile, isobornyl acetate, geranyl acetate, dimethylbenzylcarbinyl acetate, styralyl acetate, cedryl acetate, terpinyl acetate, p-tert-butylcyclohexyl acetate, vetiveryl acetate, benzyl acetate, linalyl acetate, isopentyl salicylate, benzyl salicylate, sandal wood oil, santalol, cyclamen aldehyde, cyclopentadecanolide, methyl dihydrojasmonate, dihydromyrcenol, Jasmine Absolute, jasmine lactone, cis-jasmone, citral, citronellol, citronellal, cinnamon bark oil, 1,8-cineole, cinnamaldehyde, Styrax resinoid, cedar wood oil, cedrene, cedrol, celery seed oil, thyme oil, damascone, damascenone, thymol, tuberose absolute, decanal, decalactone, terpineol, γ-terpinene, triplal, nerol, nonanal, 2,6-nonadienol, patchouli alcohol, Vanilla Absolute, vanillin, basil oil, patchouli oil, hydroxycitronellal, α-pinene, piperitone, phenethyl alcohol, phenylacetoaldehyde, petitgrain oil, hexylcinnamaldehyde, cis-3-hexenol, Peruvian balsam, vetiver oil, vetiverol, peppermint oil, pepper oil, heliotropin, Bergamot oil, benzyl benzoate, borneol, myrrh resinoid, musk ketone, methylnonylacetoaldehyde, γ-methylionone, menthol, l-menthol, l-menthone, *eucalyptus* oil, β-ionone, lime oil, lavender oil, d-limonene, linalool, lyral, lilial, lemon oil, Rose Absolute, rose oxide, rose oil, rosemary oil, and various refined oils.

Preferred examples of the dyestuff, the colorant, the dye, and the pigment include legal dyestuffs such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow 201, Yellow 202-1, Yellow 202-2, Yellow 203, Yellow 204, Yellow 205, Yellow 4, Yellow 401, Yellow 402, Yellow 403-1, Yellow 404, Yellow 405, Yellow 406, Yellow 407, and Yellow 5; Acid Red 14 and other acid dyes; basic dyes such as Arianor Sienna Brown, Arianor Madder Red, Arianor Steel Blue, and Arianor Straw Yellow; nitro dyes such as HC Yellow 2, HC Yellow 5, HC Red 3, 4-hydroxypropylamino-3-nitrophenol, N,N'-bis(2-hydroxyethyl)-2-nitro-p-phenylenediamine, HC Blue 2, and Basic Blue 26; disperse dyes; inorganic white pigments such as titanium dioxide and zinc oxide; inorganic red-based pigments such as iron oxide (red iron oxide) and iron titanate; inorganic brown-based pigments such as γ-ferric oxide; inorganic yellow-based pigments such as yellow iron oxide and ocher; inorganic black-based pigments such as black iron oxide and black lower-order titanium oxide; inorganic violet-based pigments such as mango violet and cobalt violet; inorganic green-based pigments such as chromium oxide, chromium hydroxide, and cobalt titanate; inorganic blue-based pigments such as ultramarine and Prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metal powder pigments such as aluminum powder, copper powder, and gold; surface-treated inorganic and metal powder pigments; organic pigments such as a zirconium, barium, or aluminum lake; surface-treated organic pigments; natural dyestuffs and dyes such as anthraquinones such as astaxanthin and alizarin, naphthoquinones such as β-carotene, catenal, capsanthin, chalcone, carthamin, quercetin, crocin, chlorophyll, curcumin, cochineal, and shikonin, bixin, flavones, betacyanidine, henna, hemoglobin, lycopene, riboflavin, and rutin; oxidation dyes and couplers such as p-phenylenediamine, toluene-2,5-diamine, o-, m-, or p-aminophenol, m-phenylenediamine, 5-amino-2-methylphenol, resorcin, 1-naphthol, and 2,6-diaminopyridine, and salts thereof; naturally oxidized-type dyes such as indoline; and dihydroxyacetone.

Preferred examples of the antiphlogistic agent and the antiinflammatory agent include glycyrrhizic acid and derivatives thereof; glycyrrhetic acid derivatives; salicylic acid derivatives; hinokitiol; guaiazulene; allantoin; indomethacin; ketoprofen; ibuprofen; diclofenac; loxoprofen; Celecoxib; Infliximab; Etanercept; zinc oxide; hydrocortisone acetate; prednisone; diphenhydramine hydrochloride; chlorpheniramine maleate; and plant extracts such as peach leaf extract and *Artemisia princeps* leaf extract.

Preferred examples of the antiasthmatic agent, the antichronic obstructive pulmonary disease agent, the antiallergic agent, and the immunomodulators include aminophylline, theophyllines, steroids (fluticasone, beclomethasone, and the like), leukotriene antagonists, thromboxane inhibitors, intal β-2 stimulants (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporine, sirolimus, methotrexate, cytokine regulating agents, interferon, omalizumab, and protein/antibody formulations.

Preferred examples of the anti-infectious disease agent and the antifungal agent include oseltamivir and zanamivir, and itraconazole. In the composition of the dispersion of the present invention, there may be blended as additives other than the above additives, publicly known ingredients for cosmetics, medicines, and foods such as ingredients described in the Japanese Standards of Cosmetic Ingredients, the Japanese Cosmetic Ingredients Codex, the Japan Cosmetic Industry Association list of displayed names of ingredients, the INCI dictionary (the International Cosmetic Ingredient Dictionary and Handbook), the Japanese Standards of Quasi-drug Ingredients, the Japanese Pharmacopoeia, the Japanese Pharmaceutical Excipients, and the Japan's Specifications and Standards for Food Additives, and ingredients described in Patent Publications and Patent Unexamined Application Publications (including Japanese or each language Translation of PCT International Application Publications and Re-publications of PCT International Publications) of Japan and various other countries that are classified by the International Patent Classification into the classes A61K7 and A61K8, in a publicly known combination and in a publicly known blending ratio/blending amount.

<Method for Forming Hydrogel>

In the present invention, by using the above-described dispersion, that is, a dispersion containing a lipid peptide type compound, a dissolution accelerator, a polyhydric alcohol, and a polymer emulsifier, and a dispersion further containing a heat resistance improver, a hydrogel can be formed by the following processes.

a) a process of adding the above dispersing agent to water and heating the resultant mixture at a temperature of room temperature or higher and lower than 100° C.

b) a process of cooling down the mixture with stirring until the temperature of the mixture becomes lower than the temperature in the heating process.

The above-described additive for cosmetics or additive for quasi-drugs can be added to water simultaneously together with the dispersing agent in the process a).

In the process a), the temperature for heating is preferably 50° C. to 90° C. and more preferably 60° C. to 90° C., for example 70° C. or 80° C. Preferably, the mixture is stirred while heating the mixture.

In the process a), although the time for heating and stirring the mixture is not particularly limited, for example, the time for heating is 6 hours immediately after the addition of the dispersing agent, preferably can be appropriately selected from between 30 minutes to 3 hours after the addition of the dispersing agent.

Subsequently to the process a), a process b) of cooling down the mixture with stirring until the temperature of the mixture becomes lower than the temperature in the process a), is performed.

Here, the temperature to which the mixture is cooled down is room temperature to 80° C., preferably room temperature to 40° C.

<Hydrogel>

The hydrogel formed using the above dispersion and the gel obtained by the above production method are also within the scope of the present invention.

EXAMPLES

Hereinafter, the present invention is described in detail referring to Examples and Test Examples that should not be construed as limiting the present invention.

Synthesis Example 1: Synthesis of Lipid Peptide
(N-Palmitoyl-Gly-His)

The lipid peptide used as the gelator in the present example was synthesized by the method described below.

Into a 500 mL four-neck flask, 14.2 g (91.6 mmol) of histidine, 30.0 g (91.6 mmol) of N-Palmitoyl-Gly-methyl, and 300 g of toluene were charged and thereto, 35.3 g (183.2 mmol) of a 28% methanol solution with sodium methoxide as a base was added, followed by heating the resultant reaction mixture on an oil bath at 60° C. and stirring the reaction mixture for 1 hour. Then, the oil bath was removed and the reaction mixture was left to be cooled down to 25° C. The reaction mixture was subjected to reprecipitation in 600 g of acetone and the resultant precipitate was filtered. The obtained solid was dissolved in a mixed solution of 600 g of water and 750 g of methanol and to the resultant solution, 30.5 mL (183.2 mmol) of a 6N hydrochloric acid was added to neutralize the solution to deposit a solid, followed by filtering the solid. Then, the obtained solid was dissolved in a mixed liquid of 120 g of tetrahydrofuran and 30 g of water at 60° C. and to the resultant solution, 150 g of ethyl acetate was added, followed by cooling down the resultant mixture from 60° C. to 30° C. Then, a deposited solid was filtered. Furthermore, the obtained solid was dissolved in a solvent of 120 g of tetrahydrofuran and 60 g of acetonitrile and the resultant solution was heated to 60°

C., followed by stirring the solution for 1 hour. Then, the solution was cooled down and the resultant precipitate was filtered. The obtained solid was washed with 120 g of water and the solid was filtered, followed by drying the solid under reduced pressure to obtain 26.9 g (yield: 65%) of a white crystal of an N-Palmitoyl-Gly-His free form (hereinafter, called also merely Pal-GH).

Example 1 to Example 6, Comparative Example 1: Preparation of Dispersions Using Various Dissolution Accelerators and Evaluation of Dispersibility Thereof Into a sample tube (No. 7; manufactured by Maruemu Corporation), the Pal-GH obtained by the above Synthesis Example and one of various dissolution accelerators shown in Table 1 were weighed and charged so that the composition of the mixture became the composition (mass: g) shown in Table 1, and the resultant mixture was heated and stirred in a water bath set at about 80° C. to obtain a Pal-GH dispersion.

Then, the dispersibility of the Pal-GH after heating and stirring the mixture at 80° C. was visually evaluated according to such a criterion that a dispersion in which the Pal-GH powder was homogeneously dispersed (a transparent solution was obtained) was evaluated as ○ and a dispersion in which the Pal-GH powder was not homogeneously dispersed (for example, a whitish dispersion including a lump of the Pal-GH powder) was evaluated as X.

The obtained results are also shown in Table 1.

TABLE 1

| Composition | Example | | | | | | Comparative Example |
|---|---|---|---|---|---|---|---|
| (mass: g) | 1 | 2 | 3 | 4 | 5 | 6 | 1 |
| Pal-GH | 0.070 | 0.070 | 0.070 | 0.070 | 0.070 | 0.070 | 0.070 |
| NIKKOL AM-301 | 0.215 | | | | | | |
| AMPHITOL 86B | | 0.215 | | | | | |
| AMPHITOL 20AB | | | 0.215 | | | | |
| AMPHITOL 20HD | | | | 0.215 | | | |
| AMPHITOL 20BS | | | | | 0.2.15 | | |
| LPC-1 | | | | | | 0.215 | |
| Water | 0.715 | 0.715 | 0.715 | 0.715 | 0.715 | 0.930 | 0.930 |
| Solubility during heating at 80° C. | ○ | ○ | ○ | ○ | ○ | ○ | x |

*NIKKOL AM-301: lauryldimethyl aminoacetic acid betaine manufactured by Nikko Chemicals Co., Ltd,
AMPHITOL 86B: stearyl betaine manufactured by Kao Corporation
AMPHITOL 20AB: lauramidopropyl betaine manufactured by Kao Corporation
AMPHITOL 20HD: lauryl hydroxy sulfobetaine manufactured by Kao Corporation
AMPHITOL 20BS: lauryl betaine manufactured by Kao Corporation
LPC-1: egg yolk lysolecithin manufactured by Kewpie Corporation Example 7 to Example 10: Preparation of Dispersion Using Polyhydric Alcohol and Heat Resistance Improver and Evaluation of Dispersibility Thereof Into a sample tube (No. 7; manufactured by Maruemu Corporation), the Pal-GH obtained by the above Synthesis Example and a dissolution accelerator, a polyhydric alcohol, and a heat resistance improver shown in Table 2 were weighed and charged so that the composition of the mixture became the composition (mass: g) shown in Table 2, and the resultant mixture was heated and stirred in a water bath set at 80° C. to obtain a Pal-GH dispersion.

Then, the dispersibility of the Pal-GH after heating and stirring the mixture at 80° C. was visually evaluated according to such a criterion that a dispersion in which the Pal-GH powder was homogeneously dispersed (a transparent solution was obtained) was evaluated as ○ and a dispersion in which the Pal-GH powder was not homogeneously dispersed (for example, a whitish dispersion including a lump of the Pal-GH powder) was evaluated as x.

The obtained results are also shown in Table 2.

TABLE 2

| Composition | Example | | | |
|---|---|---|---|---|
| (mass: g) | 7 | 8 | 9 | 10 |
| Pal-GH | 0.100 | 0.100 | 0.150 | 0.100 |
| AMPHITOL20HD | 0.300 | 0.300 | 0.300 | 0.300 |
| 1,3-BG | 1.00 | 1.00 | 1.00 | 1.00 |
| NIKKOL, MGS-AV | | 0.020 | | |
| Lauryl alcohol | | | 0.020 | |
| NIKKOL MGS-F75V | | | | 0.020 |
| Water | 4.40 | 4.40 | 4.00 | 4.40 |
| Solubility during heating (Soluble: o, Insoluble: x) | ○ | ○ | ○ | ○ |

*AMPHITOL20HD: lauryl hydroxy sulfobetaine manufactured by Kao Corporation
1,3-BG: 1,3-butylene glycol manufactured by ITO Inc.
Lauryl alcohol: manufactured by Kao Corporation
NIKKOI, MGS-AV: glyceryl monostearate manufactured by Nikko Chemicals Co., Ltd.
NIKKOL MGS-F75: glyceryl monostearate containing 75% of monoglyceride manufactured by Nikko Chemicals Co., Ltd.

Example 11 and Example 12: Gelation Test by Using Pal-GH Dispersion and Propylene Glycol Alginate in Combination Into a 300 mL tall beaker, as shown in Table 3, pure water and propylene glycol alginate (called also PG alginate) were charged and the resultant mixture was heated and stirred at 70° C. The stirring was performed using LABORATORY HIGH MIXER manufactured by AS ONE Corporation at 200 rpm.

Then, 1.00 g of the Pal-GH dispersion of Example 1 or Example 4 that was heated to 70° C. was added thereto and the resultant mixture was further heated and stirred for 5 minutes.

After the stop of the heating, the mixture was stirred and cooled down until the temperature of the mixture reached around 40° C. and it was confirmed whether a gel was formed. The confirmation of the formation of the gel was performed by the test tube inversion method and a state in which the fluidity of the dispersion was lost and when the tall beaker was inverted, the dispersion did not flow down was evaluated as "gelled (○)". On the contrary, a state in which no gel formation was observed was evaluated as "x". The final composition after the gelation test and the obtained test results are shown in Table 3.

TABLE 3

| Composition (% by mass) | | Example 11 | Example 12 |
|---|---|---|---|
| Dispersion | Dispersion of Example 1 | 1.00 | |
| | Dispersion of Example 4 | | 1.00 |
| PG alginate | | 0.30 | 0.30 |
| Water | | 98.70 | 98.70 |
| Gelation | | ○ | ○ |

Example 13 to Example 16: Confirmation of Effect of Heat Resistance Improver Into a 300 mL tall beaker, as shown in Table 4, pure water and propylene glycol alginate were charged and the resultant mixture was heated and stirred at 70° C. The stirring was performed using LABORATORY HIGH MIXER manufactured by AS ONE Corporation at 200 rpm.

Then, each of the Pal-GH dispersions of Examples 7 to 10 that were heated to 70° C. was added thereto in the amount shown in Table 4 and the resultant mixtures were each further heated and stirred for 5 minutes.

After the stop of the heating, the mixture was stirred and cooled down until the temperature of the mixture reached around 40° C. and it was confirmed whether a gel was formed. The confirmation of the formation of the gel was performed by the test tube inversion method and a state in which the fluidity of the dispersion was lost and when the tall beaker was inverted, the dispersion did not flow down was evaluated as "gelled (○)". On the contrary, a state in which no gel formation was observed was evaluated as "x". The final composition after the gelation test and the obtained test results are shown in Table 4.

After a portion of the resultant gel was put into a sample tube No. 7 (Maruemu Corporation) and stored at 40° C. overnight, whether insoluble matters were present in the gel was visually evaluated according to such a criterion that a dispersion containing no insoluble matters was evaluated as "thermally stable at 40° C. (○)" and a dispersion containing insoluble matters was evaluated as "not thermally stable at 40° C. (x)". The obtained results are also shown in Table 4.

TABLE 4

| Composition (% by mass) | | Example 13 | Example 14 | Example 15 | Example 16 |
|---|---|---|---|---|---|
| Dispersion | Dispersion of Example 7 | 5.80 | | | |
| | Dispersion of Example 8 | | 5.82 | | |
| | Dispersion of Example 9 | | | 5.47 | |
| | Dispersion of Example 10 | | | | 5.82 |
| PG alginate | | 0.30 | 0.30 | 0.30 | 0.30 |
| Water | | 93.90 | 93.88 | 94.23 | 93.88 |
| Gelation | | ○ | ○ | ○ | ○ |
| Thermal stability at 40° C. of the resultant gel | | x | ○ | ○ | ○ |

The invention claimed is:

1. A dispersion comprising the following components:
    a lipid peptide type compound in which a peptide portion formed by repetition of at least two or more identical or different amino acids is bonded to a lipid portion including a $C_{10-24}$ aliphatic group;
    a dissolution accelerator having, in molecules thereof, a hydrophilic portion and a hydrophobic portion, the hydrophilic portion having a betaine structure;
    water; and
    a polyhydric alcohol including at least one member selected from the group consisting of 1,3-butylene glycol, propylene glycol, and glycerin.

2. The dispersion according to claim 1, wherein the lipid peptide type compound contains at least one of compounds of Formula (1) to Formula (3) and pharmaceutically acceptable salts of the compounds:

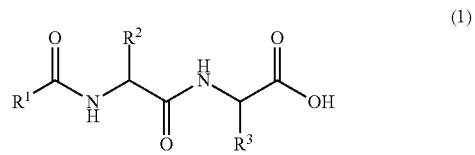

(1)

where
$R^1$ is a $C_{9-23}$ aliphatic group,
$R^2$ is a hydrogen atom or a $C_{1-4}$ alkyl group optionally having a $C_{1-2}$ branching chain,
$R^3$ is a —$(CH_2)_n$—X group,
n is a number of 1 to 4, and
X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s);

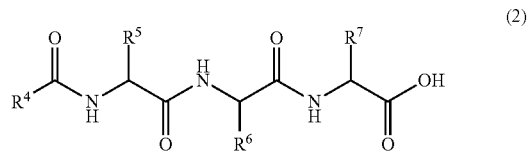

(2)

where
$R^4$ is a $C_{9-23}$ aliphatic group,
$R^5$ to $R^7$ are each independently a hydrogen atom, a $C_{1-4}$ alkyl group optionally having a $C_{1-2}$ branching chain, or a —$(CH_2)_n$—X group,
n is a number of 1 to 4, and
X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s); and

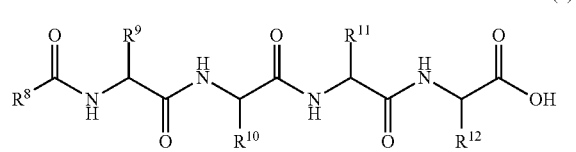

(3)

where
R⁸ is a $C_{9-23}$ aliphatic group,
R⁹ to R¹² are each independently a hydrogen atom, a $C_{1-4}$ alkyl group optionally having a $C_{1-2}$ branching chain, or a —$(CH_2)_n$—X group,
n is a number of 1 to 4, and
X is an amino group, a guanidino group, a —$CONH_2$ group, or a 5-membered ring optionally having 1 to 3 nitrogen atom(s), a 6-membered ring optionally having 1 to 3 nitrogen atom(s), or a fused heterocyclic ring composed of a 5-membered ring and a 6-membered ring optionally having 1 to 3 nitrogen atom(s).

3. The dispersion according to claim 1, wherein the dissolution accelerator is at least one selected from lauryldimethyl aminoacetic acid betaine, lauramidopropyl betaine, lauryl hydroxy sulfobetaine, stearyl betaine, and lysophosphatidylcholine.

4. The dispersion according to claim 1, further comprising a polymer emulsifier, wherein the lipid peptide type compound serves as a gelator.

5. The dispersion according to claim 4, wherein the dispersion is a premix for preparing a cosmetic or a quasi-drug.

6. The dispersion according to claim 1, wherein the dispersion is a thickener for an antifreezing fluid.

7. The dispersion according to claim 4, wherein the polymer emulsifier is at least one polymer compound selected from the group consisting of
a graft polymer compound in which a hydrophobic moiety is grafted to a hydrophilic backbone, and
a block polymer compound containing a hydrophobic structural unit and a hydrophilic structural unit.

8. The dispersion according to claim 7, further comprising a heat resistance improver.

9. The dispersion according to claim 8, wherein the heat resistance improver is
at least one higher alcohol selected from the group consisting of $C_{10-20}$ saturated and unsaturated higher alcohols; or
at least one higher fatty acid ester selected from the group consisting of $C_{10-20}$ saturated and unsaturated higher fatty acid esters.

10. The dispersion according to claim 9, wherein the heat resistance improver is cetanol, myristyl alcohol, or glyceryl monostearate.

11. The dispersion according to claim 7, wherein the polymer compound is selected from the group consisting of a carboxymethyl cellulose and an alginic acid ester.

12. The dispersion according to claim 11, wherein the polymer compound is propylene glycol alginate.

13. The dispersion according to claim 1, wherein the polyhydric alcohol is 1,3-butylene glycol.

14. The dispersion according to claim 1, wherein the polyhydric alcohol is propylene glycol.

15. The dispersion according to claim 1, wherein the polyhydric alcohol is glycerin.

16. A method for producing a hydrogel, the method comprising:
adding the dispersion as claimed in claim 4 to water and heating the resultant mixture to a temperature that is room temperature or higher and lower than 100° C.; and
cooling down the mixture with stirring until the temperature of the mixture reaches a temperature lower than the temperature in the heating to form a gel.

* * * * *